United States Patent
Kisiel et al.

(10) Patent No.: US 10,255,409 B2
(45) Date of Patent: Apr. 9, 2019

(54) SYSTEMS AND METHODS FOR IN SILICO EVALUATION OF POLYMERS

(71) Applicant: ZYMEWORKS INC., Vancouver (CA)

(72) Inventors: Kamil Kisiel, Vancouver (CA); Siddharth Srinivasan, Vancouver (CA)

(73) Assignee: ZYMEWORKS INC., Vancouver (CA)

( * ) Notice: Subject to any disclaimer, the term of this patent is extended or adjusted under 35 U.S.C. 154(b) by 271 days.

(21) Appl. No.: 14/911,505

(22) PCT Filed: Jul. 14, 2014

(86) PCT No.: PCT/CA2014/050664
§ 371 (c)(1),
(2) Date: Feb. 11, 2016

(87) PCT Pub. No.: WO2015/021540
PCT Pub. Date: Feb. 19, 2015

(65) Prior Publication Data
US 2016/0188789 A1    Jun. 30, 2016

Related U.S. Application Data

(60) Provisional application No. 61/866,466, filed on Aug. 15, 2013.

(51) Int. Cl.
| | | |
|---|---|---|
| G01N 33/48 | (2006.01) | |
| G01N 33/50 | (2006.01) | |
| G06F 19/12 | (2011.01) | |
| G06F 19/28 | (2011.01) | |
| G06F 19/16 | (2011.01) | |

(52) U.S. Cl.
CPC .............. *G06F 19/12* (2013.01); *G06F 19/28* (2013.01); *G06F 19/16* (2013.01)

(58) Field of Classification Search
None
See application file for complete search history.

(56) References Cited

U.S. PATENT DOCUMENTS

| 9,697,305 B2 | 7/2017 | Lakatos et al. | |
|---|---|---|---|
| 2003/0108870 A1* | 6/2003 | Ji | C12Q 1/6846 |
| | | | 435/6.18 |
| 2008/0261820 A1 | 10/2008 | Iyengar et al. | |
| 2012/0095743 A1 | 4/2012 | Flohil | |
| 2016/0034616 A1 | 2/2016 | Lakatos et al. | |

FOREIGN PATENT DOCUMENTS

| WO | WO 02/063479 A1 * | 8/2002 |
|---|---|---|
| WO | WO 2015/021540 | 2/2015 |

OTHER PUBLICATIONS

Brooks et al., "CHARMM: A Program for Macromolecular Energy, Minimization, and Dynamics Calculations." J. Comp. Chem., 4, 187-217 (1983).
Chin et al., "An Expanded Eukaryotic Genetic Code." Science 301, 964 (2003).
Chin et al., "Progress Toward an Expanded Eukaryotic Genetic Code." Chemistry & Biology 10, 511 (2003).
Dahiyat et al., "Probing the role of packing specificity in protein design" PNAS 94:10172-10177 (1997).
Desmet et al., "The dead-end elimination theorem and its use in protein side-chain position", Nature 356: 539-542 (1992).
Dunbrack and Karplus, "Backbone-dependent rotamer library for proteins. Application to side chain prediction", J. Mol. Biol. 230: 543-574 (1993).
Gohlke et al., "Insights into protein-protein binding by binding free energy calculation and free energy decomposition for the Ras-Raf and Ras-RalGDS complexes", Journal of Molecular Biology 330:891-913 (2003).
Goldstein, "Efficient rotamer elimination applied to protein side chains and related spin glasses", Biophys. J. 66: 1335-1340 (1994).
Jenkins, "Glossary of Basic Terms in Polymer Science," Pure Appl. Chem. 68 (12): 2287-2311 (1996).
Lasters et al., "Enhanced dead-end elimination in the search for the global minimum energy conformation of a collection of protein side chains", Protein Eng. 8: 815-822 (1995).
Leach and Lemon, 1998, "Exploring the Conformational Space of Protein Side Chains Using Dead-End Elimination and the A* Algorithm", Proteins: Structure, Function, and Genetics 33: 227-239 (1998).
Seeliger and L. de Groot, "Atomic contacts in protein structures. A detailed analysis of atomic radii, packing, and overlaps", Proteins-Structure Function and Bioinformatics 68:591-601 (2007).
Shapovalov and Dunbrack, "A smoothed backbone-dependent rotamer library for proteins derived from adaptive kernel density estimates and regressions," Structure 19, 844-858 (2011).
Simon et al., Proceedings of the National Academy of Sciences USA, 89, 9367 (1992).

* cited by examiner

*Primary Examiner* — Russell S Negin
(74) *Attorney, Agent, or Firm* — Morgan, Lewis & Bockius LLP; Brett Lovejoy

(57) ABSTRACT

Systems and methods for evaluating a polymer make use of a workflow request identifying input data and a workflow instance. The workflow instance comprises a plurality of actors, each having one or more input and output ports. The workflow instance defines an acyclic directed graph comprising nodes and edges. Each node is an actor in the plurality of actors and each edge corresponds to at least one of (i) an input port of an actor in the plurality of actors and (ii) an output port of an actor in the plurality of actors. Graph parsing produces an ordered list of job requests. Each job request corresponds to an actor in the plurality of actors. An actor in the plurality of actors is executed in an order specified by the ordered list and contributes an output to another actor in the plurality of actors that is specified by the graph.

27 Claims, 19 Drawing Sheets

82

| | |
|---|---|
| Actor Class 1 | 202-1 |
| Input port 1 class | 204-1-1 |
| Input port 2 class | 204-1-2 |
| ⋮ | |
| Input port W class | 204-1-W |
| Multi-input port 1 class | 206-1-1 |
| ⋮ | |
| Multi-input port F class | 206-1-F |
| Output port class | 208-1 |
| Option port 1 | 210-1-1 |
| ⋮ | |
| Option port X | 210-1-X |
| Task 1 | 212-1-1 |
| ⋮ | |
| Task P | 212-1-P |
| ⋮ | |
| Actor Class Y | 202-Y |
| Input port 1 class | 204-Y-1 |
| Input port 2 class | 204-Y-2 |
| ⋮ | |
| Input port W class | 204-Y-W |
| Multi-input port 1 class | 206-Y-1 |
| ⋮ | |
| Multi-input port F class | 206-Y-F |
| Output port 1 class | 208-Y |
| Option port 1 | 210-Y-1 |
| ⋮ | |
| Option port X | 210-Y-X |
| Task 1 | 212-Y-1 |
| ⋮ | |
| Task P | 212-Y-P |

Directory tree example

- $ZYMEFLOW_PROJECT_ROOT/
  - project1/
  - project2/
    - zymeflow/
      - ffffa60e-77ea-11e2-b818-00145e5533ec/
        - logs/
          - actor1/
          - actor2/
            - 1
            - 2
          - ...
        - data/
          - actor1/
          - actor2/
            - output1/
            - output2/
              - 1
              - 2
            - postprocess1/
            - ...
  - ...

Fig. 19

SYSTEMS AND METHODS FOR IN SILICO EVALUATION OF POLYMERS

CROSS REFERENCE TO RELATED APPLICATION

This application claims priority to U.S. Provisional Patent Application No. 61/866,466, entitled "Systems and Methods for In Silico Evaluation of Polymers," filed Aug. 15, 2013, which is hereby incorporated by reference herein in its entirety.

TECHNICAL FIELD

The disclosed embodiments relate generally to systems and methods for providing a computational framework for studying the effects of polymer (e.g., proteins, nucleic acids, ribonucleic acids, polysaccharides, etc.) mutations and structural refinement of polymers.

BACKGROUND

Polymer engineering involves making mutations (atomic replacement, insertion, or deletion) to a polymer of known sequence and structure, and evaluating the effects of such mutations on the physical and biological properties of the polymer. Because of the enormous resources involved in both making such mutations and testing the effects of such mutations, efforts are directed to in silico testing as a means of limiting the number of mutations that are actually synthesized and tested in the laboratory. An example of one such approach is the systems and methods for estimating the difference in conformational flexibility between the native polymer and the derivation of the polymer (where the derivation of the polymer has the mutation) in the region near the site of the mutation that are provided in U.S. Patent Application No. 61/793,203, entitled "Systems and Methods for Identifying Thermodynamic Effects of Atomic Changes to Polymers," filed Mar. 15, 2013, which is hereby incorporated by reference herein in its entirety.

In silico testing of polymers requires substantial computing power to take into account the conformational flexibility of these polymers. Moreover, each polymer and each mutation requires much customized study, and appropriate methods for evaluating mutations are still undergoing development. Because of the need for customized study and because of the ongoing research into appropriate methods for studying polymers in silico, there are multiple applications that are invoked, often on a repeatable basis in any modeling project.

Given the above-background, what is needed are systems and methods for putting these multiple applications together in different ways (e.g., workflow), and experimenting with these different workflows. For instance, such systems and methods are needed to address questions such as whether (i) a workflow that involves running application A before application B, and then following it up with application C produces a better output than (ii) a workflow that takes the average of ten instances of application A and ten instances of application B followed by application C. Another example of the type of question for which better systems and methods are needed is the determination of whether better protein modeling is achieved by substituting out application B in a workflow for a different algorithm completely, perhaps application Z, which does the same thing as application B but has completely different internal workings.

SUMMARY

The present disclosure provides a design flow and a workflow engine to drive the design flow. The design flow allows for the execution of multiple applications, termed actors, and provides structured grammar for the inputs, outputs, and options of each of the actors in the design flow. By enforcing a structured grammar for the inputs, outputs, and actor options, authors of individual actors do not need to be familiar with the details and mechanics of the workflow engine, such as resource requirements, file management, storage and backup, design flow initiation and termination, showing workflow progress and fault tolerance. In this way, polymer engineers can spend more of their efforts on coding effective algorithms as actors and less time on the mechanics of setting up and running design flows.

An actor can be conceptualized as a box within a workflow. Multiple boxes (actors) can be connected to create a scientific workflow. Each of the actors performs a function. For instance one or more actor can perform molecular simulations on one or more polymers, other actors can compute the energy of polymers, and the like. All the different actors create a framework in which workflows are readily put together using the actors in interesting and novel ways to solve very specific problems that arise in molecular simulation pursuits. Advantageously, actors in the same workflow can be written in different programming languages. For example, in some embodiments, actors are written in Java, C, C++ or python and combined into the same workflow. This provides further convenience to molecular simulation scientists, because they can write actors in a language that is most advantageous for that particular application, provided that they adhere to the input and output workflow grammar rules.

The disclosed workflows and workflow engine allows for the creation of actors, and for their execution in the form of workflows. In this regard, the disclosed workflow engine takes care of error handling. For instance, if several of the actors that collectively belong to several different workflows are running on a cluster and a node in the cluster fails because of hardware failure, the workflow engine detects this failure and puts the workflows into a particular error state and allows a user to simply restart that workflow by submitting one command, or possibly even automatically without any input, depending on the cause of the error Advantageously, the user doesn't need to get involved in reviewing the integrity of intermediate files or other aspects of the interrupted workflows. All they have to do is simply resubmit the particular workflow that has failed, and the workflow engine restarts the workflow from the intermediate state before the failure arose.

As discussed above, the disclosed workflow engine allows polymer engineers to create and submit workflows as well as to monitor their progress. The disclosed workflow engine provides a web interface through which polymer engineers designate a workflow (e.g., by specifying a unique workflow identifier associated with the workflow) and are provided with a status update of every single actor within the designated workflow. In one example, the workflow engine provides an exemplary status indicator that indicates that an actor running in the workflow is fifty percent complete and, on this basis, that it will take another two hours to complete the actor. In this example, if the polymer engineer were to return two hours later, they would see through the web interface provide d by the workflow engine that their workflow has finished, and that the results of their workflow are ready for post-processing analysis.

One aspect of the present disclosure provides a method of evaluating a first polymer at a computer system having one or more processors and memory storing one or more programs to be executed by the one of more processors. In the method, a workflow request is received. The workflow request identifies (i) a workflow instance and (ii) input data for the workflow instance, the input data comprising a set of three-dimensional coordinates $\{x_1, \ldots, x_N\}$ for all or a portion of the first polymer. Each respective $x_i$ in $\{x_1, \ldots, x_N\}$ is a three dimensional coordinate for an atom in a first plurality of atoms in the first polymer. The workflow instance comprises a plurality of actors, each actor in the plurality of actors having at least one input port and at least one output port. The workflow instance defines an acyclic directed graph comprising a plurality of nodes and a plurality of edges. Each node in the plurality of nodes is an actor in the plurality of actors and each edge in the plurality of edges corresponds to at least one of (i) an input port of an actor in the plurality of actors and (ii) an output port of an actor in the plurality of actors. Further in the method, a workflow identifier is assigned to the workflow request. In typical embodiments, this workflow identifier uniquely identifies the workflow request. The method continues by parsing the acyclic directed graph into an ordered list of job requests. Each respective job request in the ordered list of job requests corresponds to an actor in the plurality of actors. A first actor in the plurality of actors is executed in accordance with an order specified by the ordered list of job requests. The first actor contributes to the computation of a metric associated with the first polymer. The method continues by executing a second actor in the plurality of actors upon completion of the execution of the first actor. The second actor is identified by the acyclic directed graph and a first result of the first actor is passed from an output port of the first actor to an input port of the second actor. The second actor contributes to the computation of the metric associated with the first polymer, thereby evaluating the first polymer.

Examples of workflows that can be implemented in accordance with the present disclosure include, but are not limited to packing workflow, workflows that perform conformational sampling and analysis of a single polymer, workflows that analyze the interface of polymer complexes (e.g., performing a variety of atom/residue contact analysis on that interface. Thus some workflows involve making numerous mutations to one or more polymers whereas other workflows involve no mutations, just a single input structure.

For example, a more particular aspect of the present disclosure provides a method of identifying an effect of one or more derivations of one or more polymers. The method comprises, at a computer system having one or more processors and memory storing one or more programs to be executed by the one of more processors, receiving a workflow request. The workflow request identifies (i) a workflow instance and (ii) input data for the workflow instance. The input data comprises a set of three-dimensional coordinates $\{x_1, \ldots, x_N\}$ for a first polymer or a derivation of the first polymer. Each respective $x_i$ in $\{x_1, \ldots, x_N\}$ is a three dimensional coordinate for an atom in a first plurality of atoms in the first polymer or the derivation of the first polymer. The workflow instance comprises a plurality of actors. Each actor in the plurality of actors has at least one input port and at least one output port. An actor corresponds to a particular molecular simulations algorithm that can be applied to a polymer. Each actor can have multiple identical copies of itself, all executing in parallel and independently of each other. Each such instance of an actor is called a "task", and is typically used to apply the same algorithm to multiple instances of the polymer. Typically an instance of a polymer could be a particular mutation applied to that polymer, thereby allowing high throughput "screening" of tens of thousands of mutations. The workflow instance defines an acyclic directed graph comprising a plurality of nodes and a plurality of edges. Each node in the plurality of nodes is an actor in the plurality of actors. Each edge in the plurality of edges corresponds to at least one of (i) an input port of an actor in the plurality of actors and (ii) an output port of an actor in the plurality of actors. The task inherits the connectivity of the parent actor, therefore each task of a particular actor has the exact same connectivity in the directed graph. As used herein, a reference to an "actor" means specifically the multiple parallel tasks associated with that actor. In many cases, the number of tasks associated with that actor is one, indicating that the particular algorithm does not require multiple parallel instances to be running at the same time, for example an RMSD calculation that operates on all the mutations at the same time. In some embodiments, a workflow identifier is assigned to the workflow request. In some embodiments, a workflow identifier is not assigned to the workflow request and the workflow request is tracked by other means. The acyclic directed graph is parsed into an ordered list of job requests. Each respective job request in the ordered list of job requests corresponds to an actor in the plurality of actors. A first actor in the plurality of actors is executed in accordance with an order specified by the ordered list of job requests. The first actor contributes to the computation of a metric associated with one or more derivations of the first polymer.

A second actor in the plurality of actors is then executed upon completion of the execution of the first actor. This second actor is identified by the acyclic directed graph. A first result of the first actor is passed from an output port of the first actor to an input port of the second actor. For example, the first actor passes a pointer to a file location in a directory where specified data computed by the first actor is located and that is to be used by the second actor. The second actor contributes to the computation of the metric associated with one or more derivations of the first polymer, thereby identifying an effect of one or more derivations of one or more polymers.

Another aspect of the present disclosure provides a computer system for evaluating a first polymer. The computer system comprises at least one processor and memory storing at least one program for execution by the at least one processor. The memory further comprising instructions for receiving a workflow request. The workflow request identifies (i) a workflow instance and (ii) input data for the workflow instance, the input data comprising a set of three-dimensional coordinates $\{x_1, \ldots, x_N\}$ for all or a portion of the first polymer, where each respective $x_i$ in $\{x_1, \ldots, x_N\}$ is a three dimensional coordinate for an atom in a first plurality of atoms in the first polymer. The workflow instance comprises a plurality of actors, each actor in the plurality of actors having at least one input port and at least one output port. The workflow instance defines an acyclic directed graph comprising a plurality of nodes and a plurality of edges. Each node in the plurality of nodes is an actor in the plurality of actors and each edge in the plurality of edges corresponding to at least one of (i) an input port of an actor in the plurality of actors and (ii) an output port of an actor in the plurality of actors. The memory further comprises instructions for assigning a workflow identifier to the workflow request. The memory further comprises instructions for parsing the acyclic directed graph into an ordered list of job requests, each respective job request in the ordered list of job requests corresponding to an actor in the plurality of actors. The memory further comprises instructions for executing a first actor in the plurality of actors in accordance with an order specified by the ordered list of job requests. The first actor contributes to the computation of a metric associated with the first polymer. The memory further comprises instructions for executing a second actor in the plurality of actors upon completion of the execution of the first actor. The second actor is identified by the acyclic directed graph and a first result of the first actor is passed from an output port of the first actor to an input port of the second actor. The second actor contributes to the computation of the metric associated with the first polymer.

For example, some embodiments provide a computer system for identifying an effect of one or more derivations of one or more polymers. The computer system comprises at least one processor and memory storing at least one program for execution by the at least one processor. The memory comprises instructions for receiving a workflow request. The workflow request identifies (i) a workflow instance and (ii) input data for the workflow instance. The input data comprises a set of three-dimensional coordinates $\{x_1, \ldots, x_N\}$ for a first polymer or, optionally, a derivation of the first polymer. Each respective $x_i$ in $\{x_1, \ldots, x_N\}$ is a three dimensional coordinate for an atom in a first plurality of atoms in the first polymer or the derivation of the first polymer. The workflow instance comprises a plurality of actors. Each actor in the plurality of actors has at least one input port and at least one output port. The workflow instance defines an acyclic directed graph comprising a plurality of nodes and a plurality of edges. Each node in the plurality of nodes is an actor in the plurality of actors. Each edge in the plurality of edges corresponds to at least one of (i) an input port of an actor in the plurality of actors and (ii) an output port of an actor in the plurality of actors. In typical embodiments, a workflow identifier is assigned to the workflow request. The acyclic directed graph is parsed into an ordered list of job requests. Each respective job request in the ordered list of job requests corresponds to an actor in the plurality of actors. A first actor in the plurality of actors is executed in accordance with an order specified by the ordered list of job requests. The first actor contributes to the computation of a metric associated with the first polymer or, optionally, one or more derivations of the first polymer.

In some embodiments, a second actor is executed in the plurality of actors upon completion of the execution of the first actor. The second actor is identified by the acyclic directed graph and a first result of the first actor is passed from an output port of the first actor to an input port of the second actor. The second actor contributes to the computation of the metric associated with the first polymer or, optionally, one or more derivations of the first polymer, thereby identifying an effect of one or more derivations of one or more polymers or some other metric associated with the first polymer.

Another aspect of the present disclosure provides a method of evaluating a first polymer. In this aspect, at a computer system having one or more processors and memory storing one or more programs to be executed by the one of more processors, a configuration file is received. The configuration file identifies (i) a workflow type and (ii) input data for the workflow type. The input data includes a set of three-dimensional coordinates $\{x_1, \ldots, x_N\}$ for all or a portion of the first polymer. The workflow type comprises a plurality of actors, each actor in the plurality of actors having at least one input port and at least one output port. The configuration file is parsed, thereby creating a workflow instance based on the workflow type. The workflow instance comprises an ordered list of job requests. Each respective job request in the ordered list of job requests corresponds to an actor in a plurality of actors. A first actor in the plurality of actors is executed in accordance with an order specified by the ordered list of job requests. A second actor in the plurality of actors is executed upon completion of the first actor. The second actor is identified by the acyclic directed graph and a first result of the first actor is passed from an output port of the first actor to an input port of the second actor.

In particular, another aspect of the present disclosure provides a method of identifying an effect of one or more derivations of one or more polymers. The method comprises, at a computer system having one or more processors and memory storing one or more programs to be executed by the one of more processors, receiving a configuration file. The configuration file identifies (i) a workflow type and (ii) input data for the workflow type. The input data includes a set of three-dimensional coordinates $\{x_1, \ldots, x_N\}$ for a first polymer or a derivation of the first polymer. The workflow type comprises a plurality of actors. Each actor in the plurality of actors has at least one input port and at least one output port. The configuration file is parsed thereby creating a workflow instance based on the workflow type. The workflow instance comprises an ordered list of job requests. Each respective job request in the ordered list of job requests corresponds to an actor in a plurality of actors. A first actor in the plurality of actors is executed in accordance with an order specified by the ordered list of job requests. A second actor in the plurality of actors is executed upon completion of the first actor. The second actor is identified by the acyclic directed graph and a first result of the first actor is passed from an output port of the first actor to an input port of the second actor.

Another aspect of the present disclosure provides a computer system for evaluating a first polymer. The computer system comprises at least one processor and memory storing at least one program for execution by the at least one processor. The memory further comprises instructions for receiving a workflow request. The workflow request identifies (i) a workflow instance and (ii) input data for the workflow instance. The input data comprises a set of three-dimensional coordinates $\{x_1, \ldots, x_N\}$ for all or a portion of the first polymer. Each respective $x_i$ in $\{x_1, \ldots, x_N\}$ is a three dimensional coordinate for an atom in a first plurality of atoms in the first polymer. The workflow instance comprises a plurality of actors, each actor in the plurality of actors having at least one input port and at least one output port. The workflow instance defines an acyclic directed graph comprising a plurality of nodes and a plurality of edges. Each node in the plurality of nodes is an actor in the plurality of actors and each edge in the plurality of edges corresponds to at least one of (i) an input port of an actor in the plurality of actors and (ii) an output port of an actor in the plurality of actors. A workflow identifier is assigned to the workflow request. The acyclic directed graph is parsed into an ordered list of job requests. Each respective job request in the ordered list of job requests corresponds to an actor in the plurality of actors. A first actor is executed in the plurality of actors in accordance with an order specified by the ordered list of job requests. The first actor contributes to the computation of a metric associated with the first polymer. A second actor is executed in the plurality of actors upon completion of the execution of the first actor. The second actor is identified by the acyclic directed graph and a first result of the first actor is passed from an output port of the first actor to an input port of the second actor. The second actor contributes to the computation of a metric associated with the first polymer.

In a specific embodiment, the present disclosure provides a computer system for identifying an effect of one or more derivations of one or more polymers. The computer system comprises at least one processor and memory storing at least one program for execution by the at least one processor. The memory further comprises instructions for receiving a workflow request. The workflow request identifies (i) a workflow instance and (ii) input data for the workflow instance. The input data comprises a set of three-dimensional coordinates $\{x_1, \ldots, x_N\}$ for a first polymer or a derivation of the first polymer. Each respective x, in $\{x_1, \ldots, x_N\}$ is a three dimensional coordinate for an atom in a first plurality of atoms in the first polymer or the derivation of the first polymer. The workflow instance comprises a plurality of actors. Each actor in the plurality of actors has at least one input port and at least one output port. The workflow instance defines an acyclic directed graph comprising a plurality of nodes and a plurality of edges. Each node in the plurality of nodes is an actor in the plurality of actors and each edge in the plurality of edges corresponds to at least one of (i) an input port of an actor in the plurality of actors and (ii) an output port of an actor in the plurality of actors. A workflow identifier is assigned to the workflow request in typical embodiments. The acyclic directed graph is parsed into an ordered list of job requests. Each respective job request in the ordered list of job requests corresponds to an actor in the plurality of actors. A first actor in the plurality of actors is executed in accordance with an order specified by the ordered list of job requests. The first actor contributes to the computation of a metric associated with one or more derivations of the first polymer. A second actor in the plurality of actors is executed upon completion of the execution of the first actor. The second actor is identified by the acyclic directed graph. A first result of the first actor is passed from an output port of the first actor to an input port of the second actor. The second actor contributes to the computation of a metric associated with one or more derivations of the first polymer, thereby identifying an effect of one or more derivations of one or more polymers.

Still another aspect of the present disclosure provides a method of identifying an effect of a plurality of derivations of one or more polymers. The method comprises, at a computer system having one or more processors and memory storing one or more programs to be executed by the one of more processors, concurrently processing a plurality of workflow instances. A first workflow instance in the plurality of workflow instances operates on input data including a set of three-dimensional coordinates $\{x_1, \ldots, x_N\}$ for a first polymer or a derivation of the first polymer in the one or more polymers. The processing comprises executing a plurality of actors associated with the first workflow instance. Each actor in the plurality of actors has at least one input port and at least one output port. The first workflow instance defines an acyclic directed graph comprising a plurality of nodes and a plurality of edges. Each node in the plurality of nodes is an actor in the plurality of actors. Each edge in the plurality of edges corresponds to at least one of (i) an input port of an actor in the plurality of actors and (ii) an output port of an actor in the plurality of actors. The execution of the plurality of actors comprises executing actors in the plurality of actors in an order specified by the acyclic directed graph, thereby generating a plurality of metrics relating to an effect of the plurality of derivations of the one or more polymers. Metrics in the plurality of metrics are stored in respective fields of a database associated with the first workflow instance. Subsequently, responsive to a request from a user to view the plurality of metrics, each metric in the plurality of metrics is concurrently visualized in a corresponding separate graph in a plurality of graphs while at the same time listing the plurality of derivations of the first polymer in a multi-column table. The table comprises a first column for an identity of a polymer derivation and a plurality of columns, with each column being for a metric in the plurality of metrics.

Still another aspect of the present disclosure provides a computer system for identifying an effect of a plurality of derivations of one or more polymers. The computer system comprises at least one processor and memory storing at least one program for execution by the at least one processor. The memory further comprises instructions for concurrently processing a plurality of workflow instances. A first workflow instance in the plurality of workflow instances operates on input data including a set of three-dimensional coordinates $\{x_1, \ldots, x_N\}$ for a first polymer or a derivation of the first polymer. The processing comprises executing a plurality of actors associated with the first workflow instance. Each actor in the plurality of actors has at least one input port and at least one output port. The first workflow instance defines an acyclic directed graph comprising a plurality of nodes and a plurality of edges. Each node in the plurality of nodes is an actor in the plurality of actors. Each edge in the plurality of edges corresponds to at least one of (i) an input port of an actor in the plurality of actors and (ii) an output port of an actor in the plurality of actors. The execution of the plurality of actors comprises executing actors in the plurality of actors in an order specified by the acyclic directed graph, thereby generating a plurality of metrics relating to an effect of a plurality of derivations of one or more polymers. The plurality of metrics is stored in fields of a database associated with the first workflow instance. Responsive to a request from a user to view the plurality of metrics, each metric in the plurality of metrics is concurrently visualized in a corresponding separate graph in a plurality of graphs while at the same time listing the plurality of derivations of the first polymer in a multi-column table comprising a first column for an identity of a polymer derivation and a plurality of columns for the plurality of metrics.

Yet another aspect of the present disclosure provides a method of identifying an effect of a plurality of derivations of a polymer. The method comprises, at a computer system having one or more processors and memory storing one or more programs to be executed by the one of more processors, obtaining a plurality of metrics from fields of a database associated with a completed workflow instance. The completed workflow instance operated on input data including a set of three-dimensional coordinates $\{x_1, \ldots, x_N\}$ for a polymer or a derivation of the polymer by executing a plurality of actors associated with the workflow instance. Each actor in the plurality of actors has at least one input port and at least one output port, thereby generating a plurality of metrics relating to an effect of the plurality of derivations of the polymer. A plurality of graphs is displayed. Each respective graph in the plurality of graphs depicts a corresponding metric in a plurality of metrics across a plurality of derivations of the polymer. Concurrently to the display of the plurality of graphs, a listing of the plurality of derivations of the polymer is displayed in a multi-column table comprising a first column reserved for polymer derivation identity and further comprising a plurality of columns for the plurality of metrics associated with the derivation of the polymer. Responsive to receiving a first selection of a first sub-range of a first graph in the plurality of graphs, the derivations of the polymer that are listed in the multi-column table is limited to those in the first sub-range of the first graph.

Still another aspect provides a computer system for identifying an effect of a plurality of derivations in a polymer. The computer system comprises at least one processor and memory storing at least one program for execution by the at least one processor. The memory further comprises instructions for, at a computer system having one or more processors and memory storing one or more programs to be executed by the one of more processors, obtaining a plurality of metrics from fields of a database associated with a completed workflow instance. The completed workflow instance operated on input data including a set of three-dimensional coordinates $\{x_1, \ldots, x_N\}$ for a polymer or a derivation of the polymer by executing a plurality of actors associated with the workflow instance. Each actor in the plurality of actors has at least one input port and at least one output port. The completed workflow instance generates a plurality of metrics relating to an effect of the plurality of derivations of the polymer. A plurality of graphs is displayed. Each respective graph in the plurality of graphs depicts a corresponding metric in a plurality of metrics across a plurality of derivations of the polymer. Displaying concurrently with the plurality of graphs is a listing of the plurality of derivations of the polymer in a multi-column table comprising a first column reserved for polymer derivation identity and further comprising a plurality of columns for the plurality of metrics associated with the derivation of the polymer. Responsive to receiving a first selection of a first sub-range of a first graph in the plurality of graphs, the derivations of the polymer that are listed in the multi-column table are limited to those in the first sub-range of the first graph.

Another aspect provides a system for evaluating a polymer comprising (A) a first computer comprising a first memory and one or more first processors. The first computer includes non-transitory instructions for execution by the one or more first processors to schedule a plurality of workflow jobs. Each respective workflow job in the plurality of workflow jobs is associated with a corresponding workflow instance in a plurality of workflow instances. Each respective workflow instance in the plurality of workflows includes a configuration file that (i) defines a workflow type, (ii) specifies a project name, (iii) specifies one or more workflow inputs, and (iv) specifies one or more workflow outputs. Each respective workflow instance in the plurality of workflow instances defines a directed graph of workflow actions. Each respective workflow instance in the plurality of workflow instances is associated with a unique workflow identifier. The plurality of workflow instances collectively generate a plurality of data files generated in a database format, including workflow metadata. A second computer is in electronic communication with the first computer. The second computer comprises a second memory and one or more second processors. The second computer includes non-transitory instructions for execution by the one or more second processors to monitor a status of each workflow job in the plurality of workflows jobs.

In some embodiments a third computer is in electronic communication with the second computer and the first computers. This third computer comprises a third memory and one or more third processors.

In some embodiments the third computer includes non-transitory instructions for execution by the one or more third processors to read the plurality of data files in HDF5 format (e.g., release HDF5-1.8.11 or greater), and provides data derived therefrom in a serialized format for use by a post-analysis program. For more information on the HDF5 format, see Folk et al., 2011, "An overview of the HDF5 technology suite and its applications," AD'11 Proceedings of the EDBT/ICDT 2011 Workshop on Array Databases, page 26-47, ACM, New York, N.Y., USA, which is hereby incorporated by reference herein in its entirety.

In some embodiments, the third computer includes non-transitory instructions for execution by the one or more third processors to read the plurality of data files in a format such as ASCII, csv, pickled or any other format as long as an appropriate reader and writer application programming interface is available for the format, and provides data derived therefrom in a serialized format for use by a post-analysis program. For more information on the csv file format, see Network Working Group, Shafranovich, Request for Comments: 4180 SolidMatrix Technologies, Inc. Category: Informational October 2005, which is hereby incorporated by reference herein in its entirety. For more information on the pickled file format, see Beazley and Jones, 2013, "Python Cookbook", Third Edition, O'Reilly Media Inc. Sebastopol, Calif. 95472, which is hereby incorporated by reference herein in its entirety.

In some embodiments, the post-analysis program is a web based visualization application, a graphing utility, a data exploration program, or a mining framework.

In some embodiments, the system further comprises a cluster of computers in electronic communication with the first computer and the second computer, each respective computer in the cluster of computers comprising memory and one or more processors, the memory comprising non-transistory instructions for execution by the one or more processors to execute a workflow job in the plurality of workflow jobs.

BRIEF DESCRIPTION OF THE DRAWINGS

The embodiments disclosed herein are illustrated by way of example, and not by way of limitation, in the figures of the accompanying drawings. Like reference numerals refer to corresponding parts throughout the drawings.

FIG. 7 illustrates an actor class library, according to some embodiments.

FIG. 14 illustrates a listing of a plurality of derivations of a polymer in a multi-column table, responsive to the user selection of FIG. 13, the table comprising a first column reserved for polymer derivation identity and the table further comprising a plurality of columns for the plurality of metrics associated with the derivations of the polymer processed by a workflow according to some embodiments.

FIG. 19 illustrates how data is stored for each workflow according to some embodiments.

DETAILED DESCRIPTION OF THE EMBODIMENTS

Figure 1:
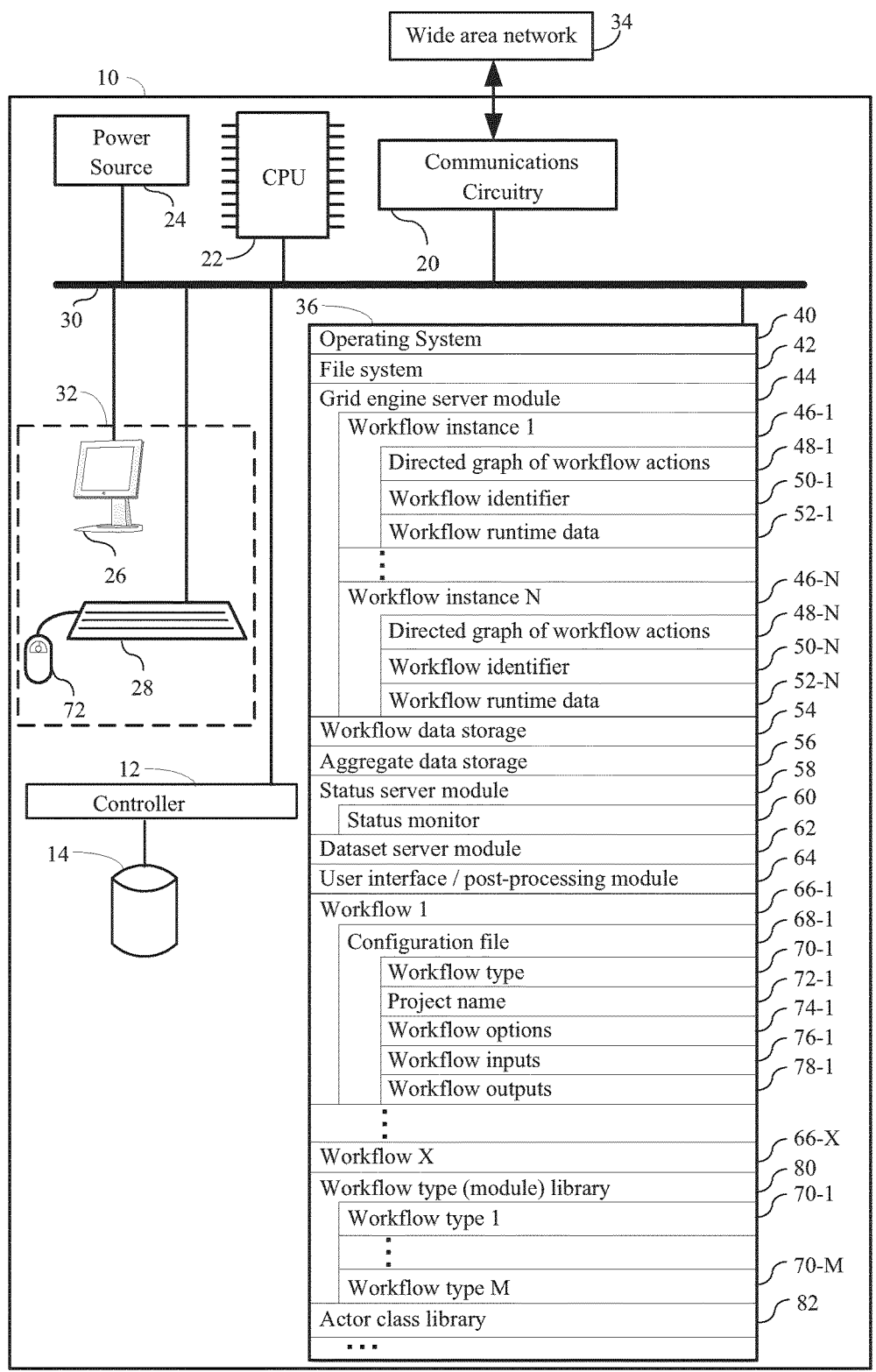
FIG. 1 is a block diagram illustrating a system for identifying an effect of one or more derivations of one or more polymers, according to some embodiments.

The embodiments described herein provide systems and methods for a workflow engine. The advantages of the disclosed workflow engine are first addressed by considering a packing workflow, which is one type of workflow supported by the disclosed workflow engine and addresses a common polymer modeling task. The packing workflow can be conceptualized as a block diagram that includes a series of blocks in series, with each block representing an actor. Each block can have multiple copies of itself, each running in parallel on a computational cluster. Each such instance of that block is a "task", which typically operates on one derivation of a polymer out of the tens of thousands that some embodiments of the workflow are configured to screen. The packing workflow addresses questions such as determining the effects of specific mutations to a polymer (e.g., protein) of interest. A protein engineer specifies the specific mutations to make to the polymer and then runs the polymer through the packing workflow, which first modifies the polymer to have the specified mutations, then optimizes the regions of the polymer surrounding the polymer in order to achieve the best (most likely) structure for the polymer containing the specified mutations, and then runs analysis actors on the resulting structure. In this way, questions such as determining the effects of specific mutations (e.g., P100G) on the electrostatics, hydrogen bonding networks, residue contacts, binding affinity and stability of the polymer are addressed. Advantageously, the packing workflow can be scaled using the workflow engine to individually analyze in this manner thousands or even tens of thousands of different mutations of a particular polymer or set of polymers. When scaled in this manner, the data generated can be represented, for example, as a two dimensional table with each row representing one tested combination of mutations, and each column representing a different metric (e.g., electrostatic energy, hydrogen bonding, residue contacts, etc.). Such a representation can provide information about tens of thousands of mutations that were run through the packing workflow.

To parse through the data generated by the disclosed workflows, the present disclosure further provides systems and methods for parsing through the workflow data and for visualizing the workflow data. They can be used to visualize the metrics from the workflow in a convenient graphical user interface, such as a web browser. In this way, a user can choose the specific metrics they're interested in by applying filters using screen toggle tools. For instance, in the case of the packing workflow, a user can use the interface to find the metrics of specific mutations from among the thousands mutations that were run through the workflow. In some embodiments, the visualization system creates a plurality of histograms (plots) for each of the metrics run in the associated workflow (e.g., the packing workflow), and then a user can go into those plots and filter out all the mutations where the electrostatic energy is over a specified threshold.

FIG. 1 provides a block diagram illustrating a workflow engine 10 according to some embodiments. The computer 10 typically includes one or more processing units (CPU's, sometimes called processors) 22 for executing programs (e.g., programs stored in memory 36), one or more network or other communication interfaces 20, memory 36, a user interface 32, which includes one or more input devices (such as a keyboard 28, mouse 72, touch screen, keypads, etc.) and one or more output devices such as a display device 26, and one or more communication buses 30 for interconnecting these components. The communication buses 30 may include circuitry (sometimes called a chipset) that interconnects and controls communications between system components.

Memory 36 includes high-speed random access memory, such as DRAM, SRAM, DDR RAM or other random access solid state memory devices; and typically includes non-volatile memory, such as one or more magnetic disk storage devices, optical disk storage devices, flash memory devices, or other non-volatile solid state storage devices. Memory 36 optionally includes one or more storage devices remotely located from the CPU(s) 22. Memory 36, or alternately the non-volatile memory device(s) within memory 36, comprises a non-transitory computer readable storage medium. In some embodiments, the non-volatile components in memory 36 include one or more hard drives 14 controlled by one or more hard drive controllers 12. In some embodiments, memory 36 or the computer readable storage medium of memory 36 stores the following programs, modules and data structures, or a subset thereof:

- an operating system 40 that includes procedures for handling various basic system services and for performing hardware dependent tasks;
- a file system 42 for handling basic file I/O tasks;
- a grid engine server module 44 for scheduling one or more workflow jobs;

one or more workflow instances 46-1, each respective workflow instance 46 explicitly or implicitly defining a directed graph of workflow actions 48, and each respective workflow instance 46 being associated with a unique workflow identifier 50 and optionally including workflow runtime data 52;

workflow data storage 54 for storing the files generated by workflow instances in a database format, including workflow metadata;

aggregate data storage 56 for storing the output of workflow instances in a database format;

a status server module 58 that includes a status monitor 60 for monitoring workflow instance 40 status;

a dataset server module 62 for parsing through aggregate data storage 56 and/or workflow data storage 54 to provide data from workflow instances 40 in a graphical format in conjunction with user interface/post-processing module 64;

a plurality of workflows 66, each workflow 66 including a configuration file 68 that (i) defines a workflow type 70, (ii) specifies a project name 72, (iii) optionally includes one or more workflow options 74, (iv) specifies one or more workflow inputs 76, and (v) specifies one or more workflow outputs 78;

a workflow type (module) library 80 that defines a plurality of workflow types 70; and an actor class library 82 which defines actors used in the workflow 66 of the present disclosure.

In some embodiments, dataset server module 62 runs on a cluster of computers that are in electronic communication with other components of the workflow engine 10. This cluster is responsible for providing the raw data generated by different actors in workflows 66 to data analysis software programs requesting this information. In some embodiments, such data analysis software programs are implemented as web-based visualization software as described below in conjunction with FIGS. 12-18. More generally, such data software programs are any programs in a general and broad class of post-processing applications. In some embodiments, the dataset server module 62, operating on the cluster of computers, retrieves workflow 46 specific metadata from the status server module 58 (also termed the central workflow server). Examples of this metadata include, but are not limited to, unique workflow ID, workflow type, and the location of the raw intermediate data from the aggregate workflow data storage 54. The dataset server module 62 comprises data readers and writers which accept this raw workflow input (e.g., metadata) and provide the raw data in a serialized format for consumption by post-processing applications. This serializable format can be a JSON representation of the data, or any other serialization protocol (cPickle, numpy arrays, text based formats, etc.). The dataset server module 62 can typically handle file formats that are standardized by the workflow 46 that generated the data. For instance, in the case of a packing workflow 46, there are two kinds of data that are accessed by the dataset server module 62: (i) numerical results of the different molecular simulation algorithms that are executed by each actor within the workflow (e.g., RMSD calculations, stability and affinity computations, potential energy and knowledge-based energy computations, solvent accessible and packing density related metrics, inter-residue and inter-atoms contacts, etc.) and different molecular structures that are typically obtained as a result of some structural refinement algorithm (e.g., molecular dynamics, Monte Carlo simulations, Dead End Elimination based rotamer pruning, etc). In some embodiments, since the software underlying the workflow 46 that generated such data is standardized to use a small subset of supported file formats (e.g., HDF5 or CSV formats for raw data, and a proprietary file format for molecular structures), enforcing these rules is accomplished without undo amounts of work. Provided that the application developer follows the standard architecture and file formats for the numerical data and the molecular structures themselves when creating a workflow 46, any workflow that involves that algorithm can be processed by dataset server module 62. Advantageously, in preferred embodiments, the dataset server module 62 does not require the use of a particular file format, as long as file formats are standardized throughout the workflow architecture generating the data to be analyzed by the dataset server module 62. Therefore moving from HDF5 based numerical data format to a completely different format in the future (say mmCIF or cPickle files) is easily accomplished by adding the corresponding reader to the dataset server module 62, rather than rewriting the software modules within the dataset server module 62. This flexibility in the dataset server module 62 and the overall system architecture advantageously allows for updates to workflow engine with new file formats, from time to time, without any requirement that the above-identified software modules be rewritten.

Advantageously, the workflow data storage 54 and/or aggregate data storage 56 is abstracted away from the final processed data from the dataset server module 62. This allows for efficient storage and backup options, since different workflows 46 can have very different requirements. In the case of the packing workflows 46, many hundreds of files are typically generated for each mutation that is part of the packing workflow. Since typically the packing workflow processes thousands of mutations in parallel, it will be readily apparent that the file servers where the data is stored are subjected to extensive input/output demands, even though the individual contents of each file is very small, typically in the order of a few hundred kilobytes. Additionally, since many of the workflow algorithms run in the space of few seconds, these multiple thousands of files are generated in a very short period of time, thereby significantly increasing the load on the file servers. Therefore any file server that handles these types of workflows is optimized for fast response times and robust file management, though sheer size of the filesystem is not an appreciable factor. In the case of a molecular dynamics based workflow, the number of files is very small, however each file may be hundreds of gigabytes in size. In this instance, the filesystem servicing such a workflow is optimized for high capacity, but performance is not as critical. The disclosed framework allows for having multiple different types of filesystems and backup protocols on a per-workflow basis. The disclosed workflow scheduling software can allocate resources based on the type of workflow, thereby optimizing the performance of each workflow depending on its needs.

Figure 10:
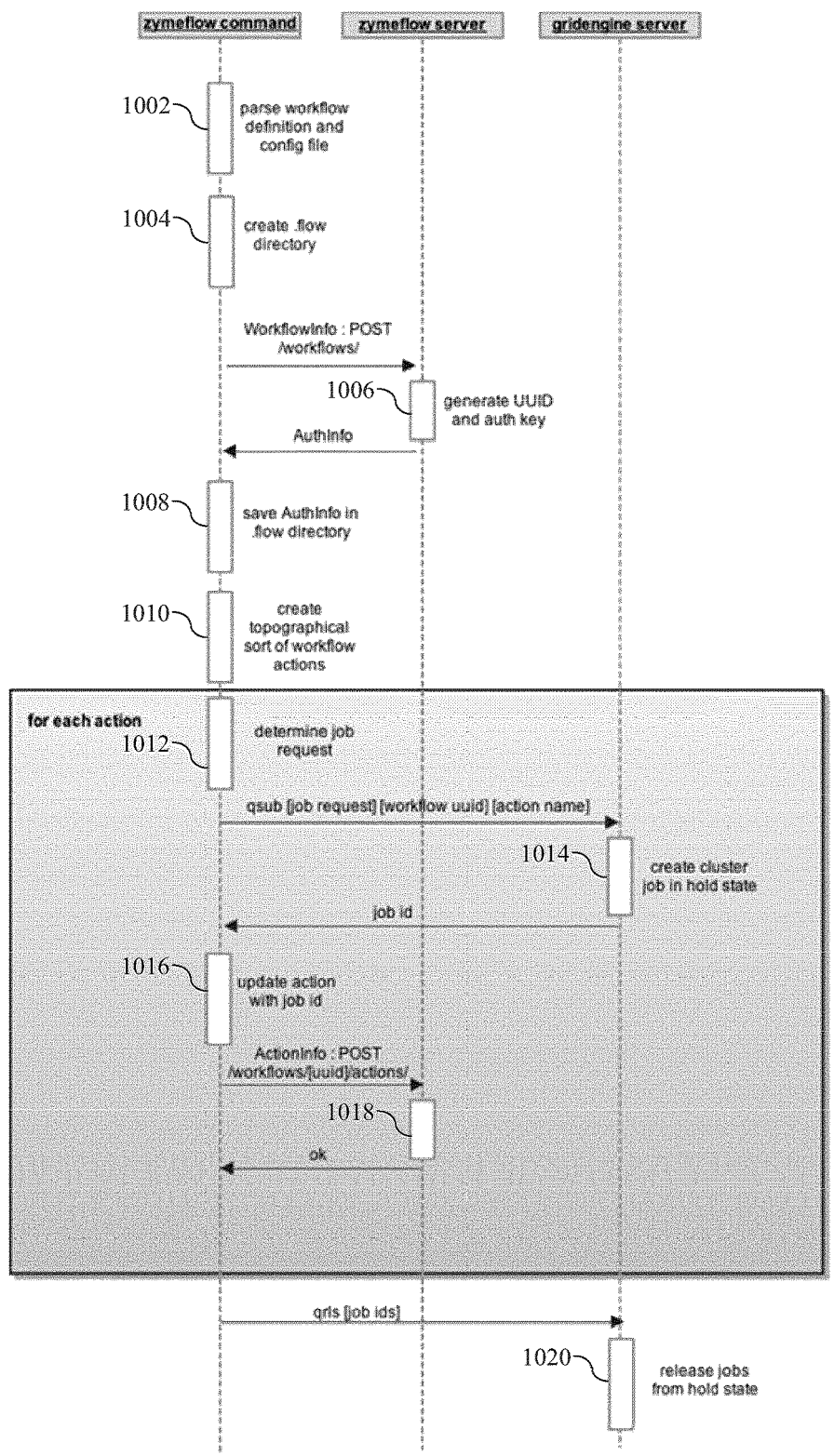
FIG. 10 provides a detailed view of actions taken when a workflow is executed, according to some embodiments.

Although not shown, in typical embodiments, one or more clients that are in electronic communication with system 10 communicate workflow requests through wide area network 34 or some other form of network to the grid engine server module 44, for instance, as described in conjunction with FIG. 10 in more detail below.

Although not shown, in typical embodiments, one or more server nodes are in electronic communication with system 10 through wide area network 34 or some other form of network so that the grid engine server module 44 can execute actors in workflows on such server nodes. For instance, in some embodiments grid engine server module 44 is in electronic communication with two or more server nodes, five or more server nodes, or ten or more server nodes and each such server node is capable of concurrently running two or more jobs corresponding to two or more actors, ten or more jobs corresponding to ten or more actors, or twenty or more jobs corresponding to twenty or more actors.

Each workflow 66 takes as input 76 the three-dimensional coordinates $\{x_1, \ldots, x_N\}$ for a polymer or a derivation of a polymer, where each respective $x_i$ in $\{x_1, \ldots, x_N\}$ is a three dimensional coordinate for an atom in a plurality of atoms in the polymer or the derivation of the polymer. In some embodiments, a polymer used as input to a workflow 66 is a protein, a polypeptide, a polynucleic acid, a polyribonucleic acid, a polysaccharide, or an assembly of any combination thereof. In some embodiments, a polymer used as input to a workflow 66 comprises between 2 and 5,000 residues, between 20 and 50,000 residues, more than 30 residues, more than 50 residues, or more than 100 residues. In some embodiments a polymer used as input to a workflow 66 has a molecular weight of 100 Daltons or more, 200 Daltons or more, 300 Daltons or more, 500 Daltons or more, 1000 Daltons or more, 5000 Daltons or more, 10,000 Daltons or more, 50,000 Daltons or more or 100,000 Daltons or more. In some embodiments, a workflow 66 takes as input multiple polymers.

In some embodiments, a workflow 66 takes as input a derivation of a polymer or itself makes one or more derivations of a polymer. In some embodiments, a derivation of a polymer is formed by incorporating any combination of atomic replacements, insertions or deletions into the polymer and structurally refining the polymer to form a structurally refined derived set of three-dimensional coordinates $\{y_1, \ldots, y_N\}$ for a derivation of the polymer. This structural refinement is optionally performed by the workflow 66 or prior to execution of the workflow 66. Each respective $y_i$ in $\{y_1, \ldots, y_N\}$ represents the position of an atom in three-dimensional space. For example, in some embodiments, the polymer is a protein, and each $y_i$ in the set of $\{y_1, \ldots, y_N\}$ is the three-dimensional coordinates of an atom in the protein.

Figure 2:
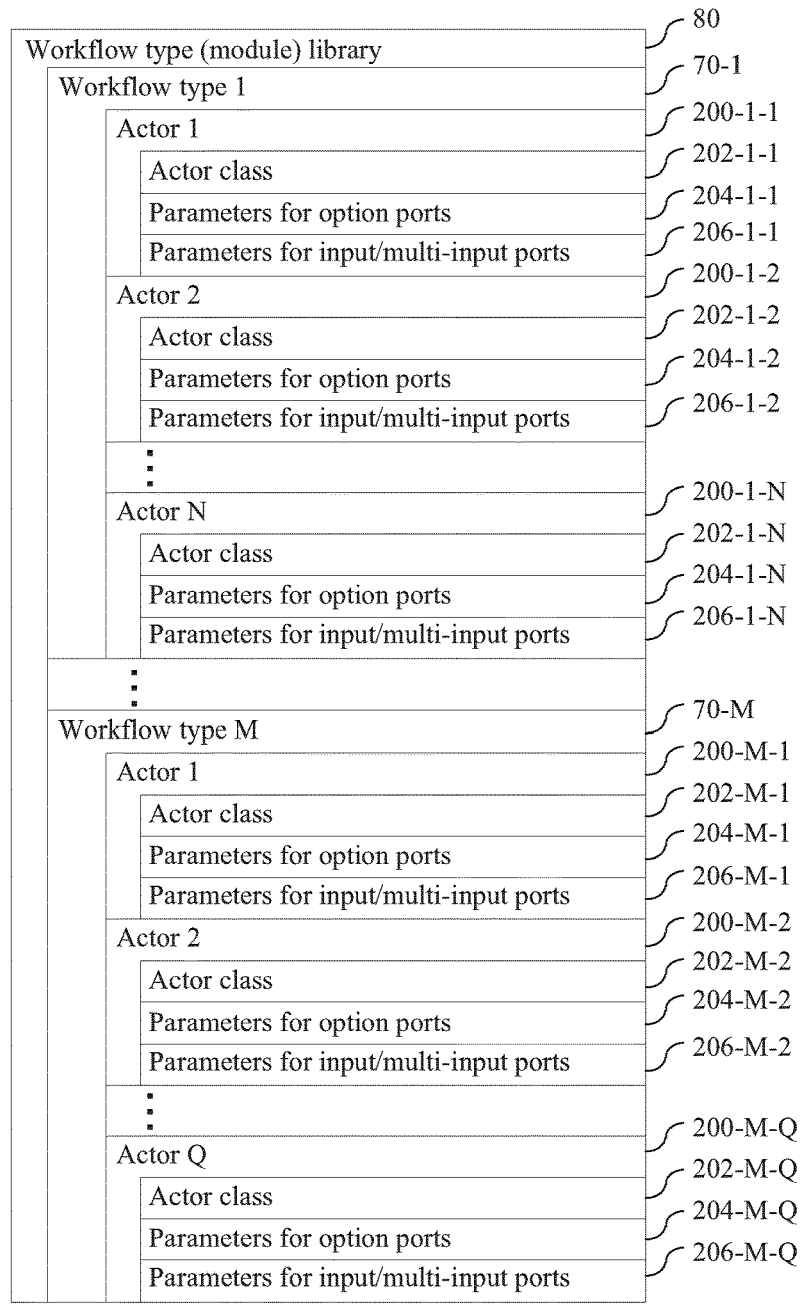
FIG. 2 illustrates a workflow type module library, according to some embodiments.

Each workflow 66 is a predefined workflow type 70 that is defined in a workflow type library 80. Referring to FIG. 2, in some embodiments, for each respective workflow type 70, the workflow type library 80 specifies which actors 200 are in the respective workflow type. In some embodiments, a workflow type 70 specifies additional information about a workflow, such as workflow options. Each actor 200 in a workflow type is itself defined in an actor class library (not shown). Accordingly, each actor 200 specifies an actor class 202.

Figure 3:
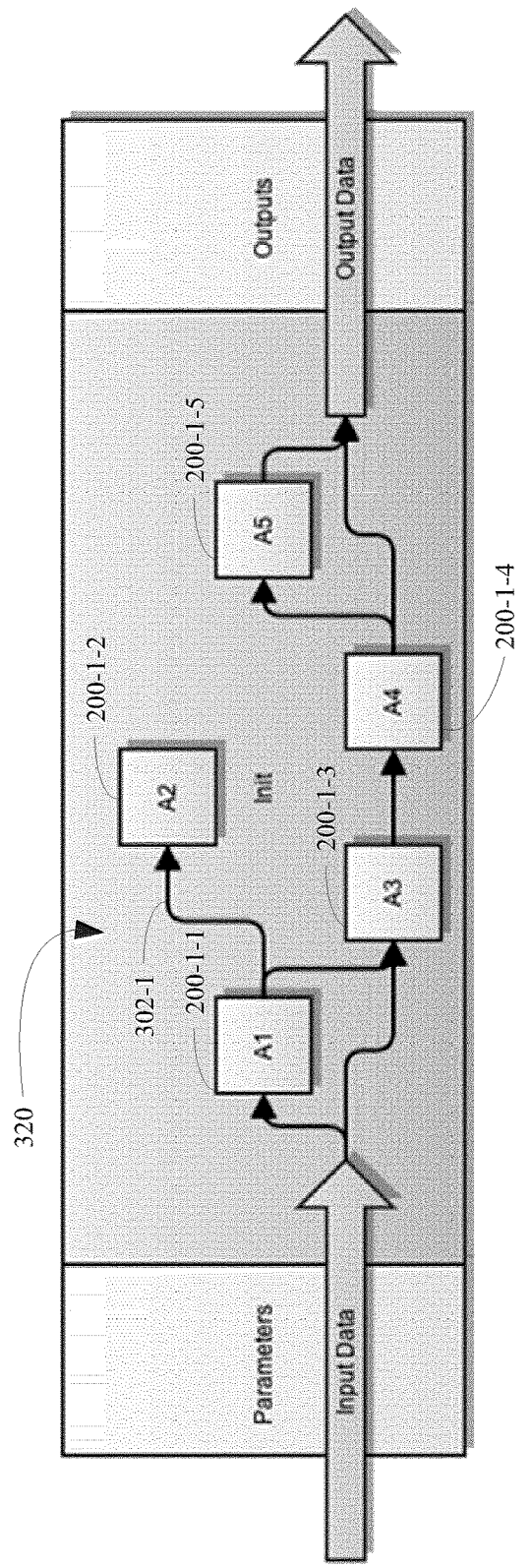
FIG. 3 illustrates an acyclic directed graph of a workflow that comprises a plurality of actors as nodes and the relationship between actor input ports and output ports as edges, according to some embodiments.

Advantageously, actors 200 within workflow types 70 are linked to each other by a defined set of input and output ports. To facilitate this linkage, each actor class 202 has a defined set of input ports, multi-input ports, output ports, and/or option ports. For actors 200 in given workflow types 70 in the workflow library 80, the parameters (e.g., parameters for option ports 204 and parameters for input/multi input ports 206) for such ports are provided. As illustrated in FIG. 3, the linkages between actors 200 within a workflow type 70 define an acyclic directed graph in which individual nodes of the graph are actors 200 of the workflow type 70 and each edge in the graph corresponds to at least one of (i) an input port of an actor 200 of the workflow type and (ii) an output port 200 of an actor in the workflow type. For example, in FIG. 3, edge 302-1 corresponds to the output port of actor 200-1-1 and an input port of actor 200-1-2. Thus, data from the output port of actor 200-1-1 is passed to the input port of actor 200-1-2.

Figure 4:
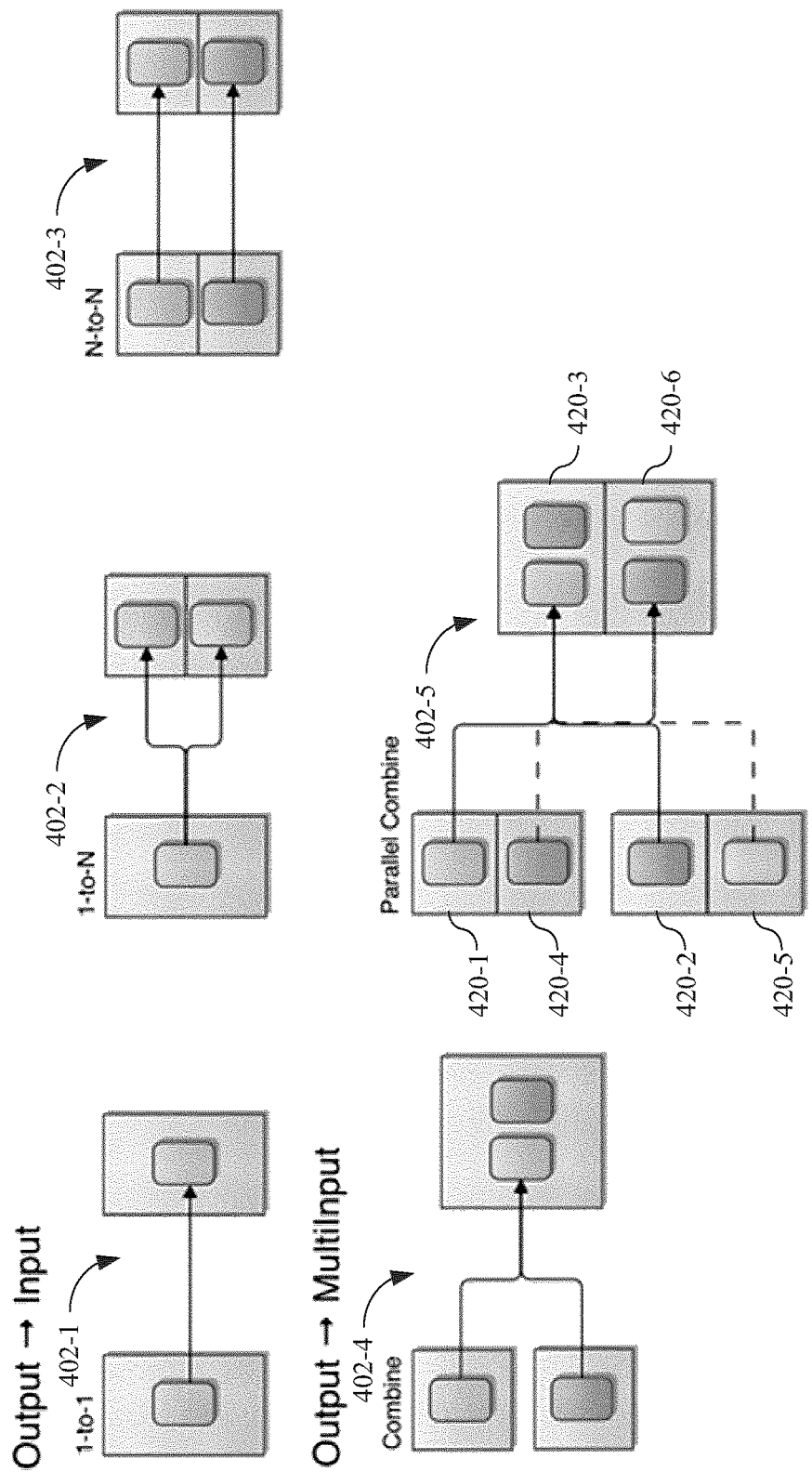
FIG. 4 illustrates exemplary relationships between actor inputs and actor outputs, according to some embodiments.

Referring to FIG. 4, actors 200 within the disclosed workflow types 70 can be arranged in any combination of a variety of manners. Panel 402-1 depicts one to one coupling in which the output of one actor is directed to the input of another actor. Panel 402-2 depicts one to N coupling in which the output of a first actor is directed to input of a plurality of actors, that is, each actor in the plurality of actors receives the output of the first actor. Panel 402-3 shows that the acyclic directed graphs of the workflow types 70 can include an N-to-N arrangement where the output of individual actors in a first plurality of actors is communicated to respective corresponding actors in a second plurality of actors in the same workflow type 70.

As FIG. 4 further illustrates, the output of a first set of actors can also be provided to a second set of actors, where the number of actors in the second set of actors is less than the number of actors in the first set of actors. For instance, panel 402-4 illustrates how the output of two different actors is provided as input to another single actor within a workflow type 70. Panel 402-5 illustrates how the output of actors 420-1 and 420-2 is provided as input to actor 420-3 while the output of actors 420-4 and 420-5 is provided as input to actor 420-6 within a workflow type 70.

Figure 5A:
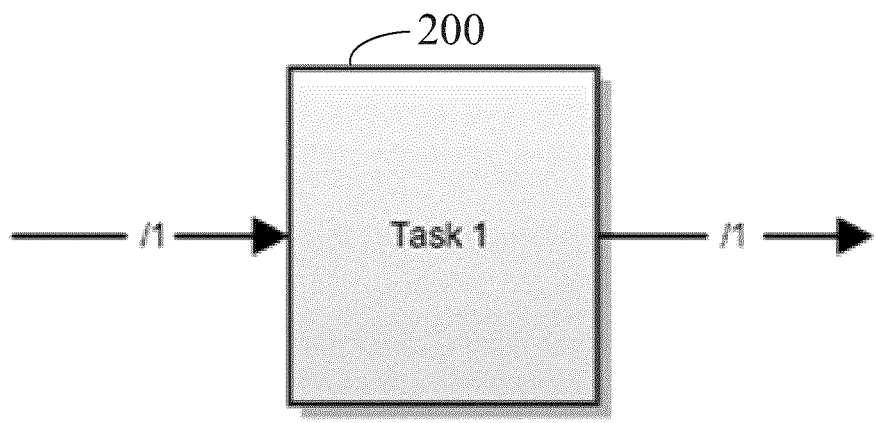
FIGS. 5A and 5B illustrate the relationship between actor input width and the number of tasks that are run by an actor, according to some embodiments.
Figure 5B:
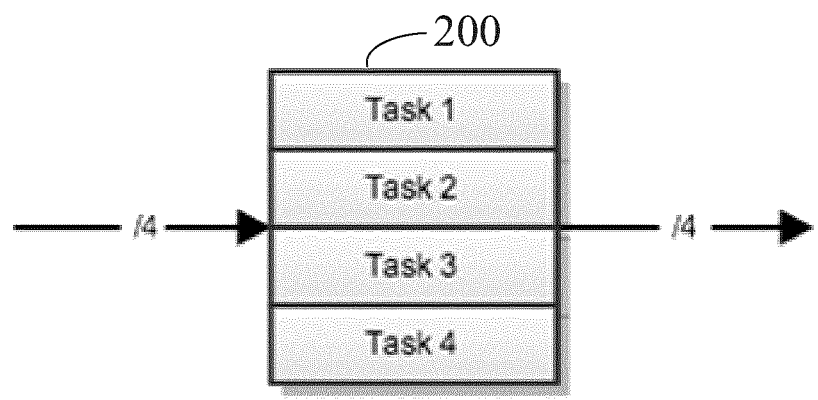

Referring to FIGS. 5A and 5B, a single data link between actors 200 can carry one or more data elements of the same type. Inside an actor 200, each element is processed in a separate task. Consequently, the number of elements in each of the actor's outputs is determined by the number of tasks that are performed within the actor. FIG. 5A illustrates the case in which the input to the actor 200 is a single element and the actor performs a single task and thus has an output width of one. FIG. 5B illustrates the case in which the input to the actor 200 consists of four elements and the actor performs four tasks and thus has an output width of four. More generally, the input to an actor 200 consists of N elements, where N is any positive integer, the actor performs N tasks, and corresponding can produce an output width of N.

Figure 6:
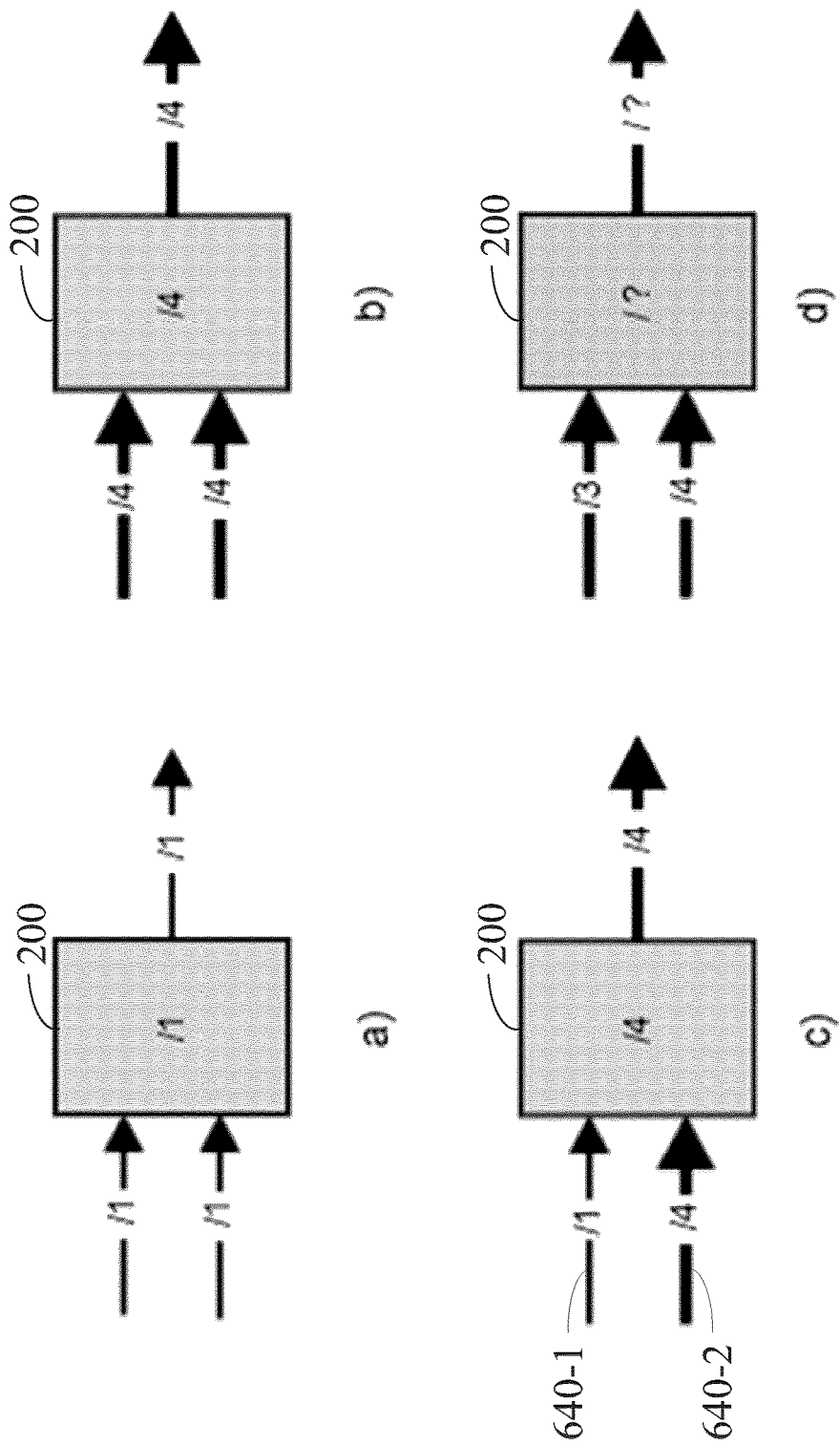
FIGS. 6A, 6B, 6C and 6D illustrate how multiple inputs of varying width are handled by actors, according to some embodiments.

Since actors can have one or more inputs of different widths from one or more different sources (e.g., other actors and/or from predetermined datapaths or from standard inputs (e.g., keyboard, etc.)), some embodiments of the present disclosure provide rules on how the number of tasks in an actor is determined. FIG. 6 illustrates. Referring to FIGS. 6a) and 6b), if the width of all inputs is N, the number of tasks performed by the actor 200 is N. Referring to 6c), if one of the input widths is N>1, then other input widths have to be either N or 1. In the example illustrated in FIG. 6c) in which one of the input widths is 1 (640-1) and one of the input widths is greater than 1 (640-2), the same data from the input of width 1 (640-1) is broadcast to every task in the actor 200. Referring to FIG. 6d), two or more inputs of mismatched width greater than one is an invalid configuration in typical embodiments.

Referring to FIG. 7, each actor class 202 used in the workflow types 70 defined in the workflow library 70 is defined in an actor class library 82. An actor class 202 defines one or more input port classes 204 and/or one or more multi-input port classes 206. In some embodiments an actor class 202 defines one or more input port class 204 and no multi-input port classes 206. In some embodiments an actor class 202 defines one, two, three, four, or five or more input port class 204 and one, two, three, four, or five or more multi-input port classes 206. In some embodiments an actor class 202 defines no input port class 204 and one or more multi-input port classes 206.

When initializing an actor 200, its input ports can be initialized with the output of another actor or with a string literal. Thus, as defined by the input port classes 204, an input port can receive either a string literal which is interpreted as a file path, or an output port from another actor 200. Each input port class 204 is of a defined file type. In preferred embodiments, input ports 204 can only receive data from an output port of the same file type. Within an actor 200, the input port 204 will return a path, e.g: accessing "ports.structure" will return a string that is the file path of a structure that can be read. For example:

```
class Foo(Actor):
    in = Input("some input", FooType)
    def execute(self, ports):
        # ports.in will be set to a file path. Usually this is passed as an argument     # to a program.
        path = ports.in
    ## in the workflow init( )
    a = flow.add(X("actorA"))
    b = flow.add(Foo("actorB", in=a.out)) # X's out must be of FooType
```

A multi-input class 206 works similarly to an input port class 204 except that it accepts a list of file path literals and/or output ports. Thus an actor 200 that uses a multi-input class 206 can aggregate the data from multiple outputs. Within an actor 200, the multi-input port defined by a multi-input class 206 will return a list of paths, e.g. accessing "ports.structures" will return a list of file paths. For example:

```
class Foo(Actor)
    in = multi-input("some multi-input", FooType)
    def execute(self, ports):
        # ports.in will be set a list of file paths.
        for path in ports.in:
            do_something(path)
    ## in the workflow init( )
    a = flow.add(X("actorA"))
    b = flow.add(Y("actorB"))
    c = flow.add(Foo("actorC", in=[a.out, b.out])) # X and Y's out must also be of FooType
```

In this case the Foo actor, c will "zip" the outputs of actors a and b. Alternatively, the actor can be assigned just one output port:
c=flow.add(Foo("actorD", in=a.out))
In this case the value of "ports.in" will be a list of paths to the outputs of a, one per task.

Continuing to refer to FIG. 7, an actor class 202 further defines an output port class 208. An output port is used for the output produced by an actor 200. In preferred embodiments, when initializing an actor in a workflow 70, no arguments are passed to the output port. In typical embodiments, each output port class 208 is one of a predetermined allowed output port classes. The following provides an example of the use of an output port in a workflow 70:

```
class Foo(Actor):
out = Output("some output", FooType)
def execute(self, ports):
# ports.out will be a file path
do_something(ports.out)
in the workflow init( )
a = flow.add(Foo("actorA"))
b = flow.add(X("actorB", in=a.out)) # X's in must also be of FooType
```

Figure 11:
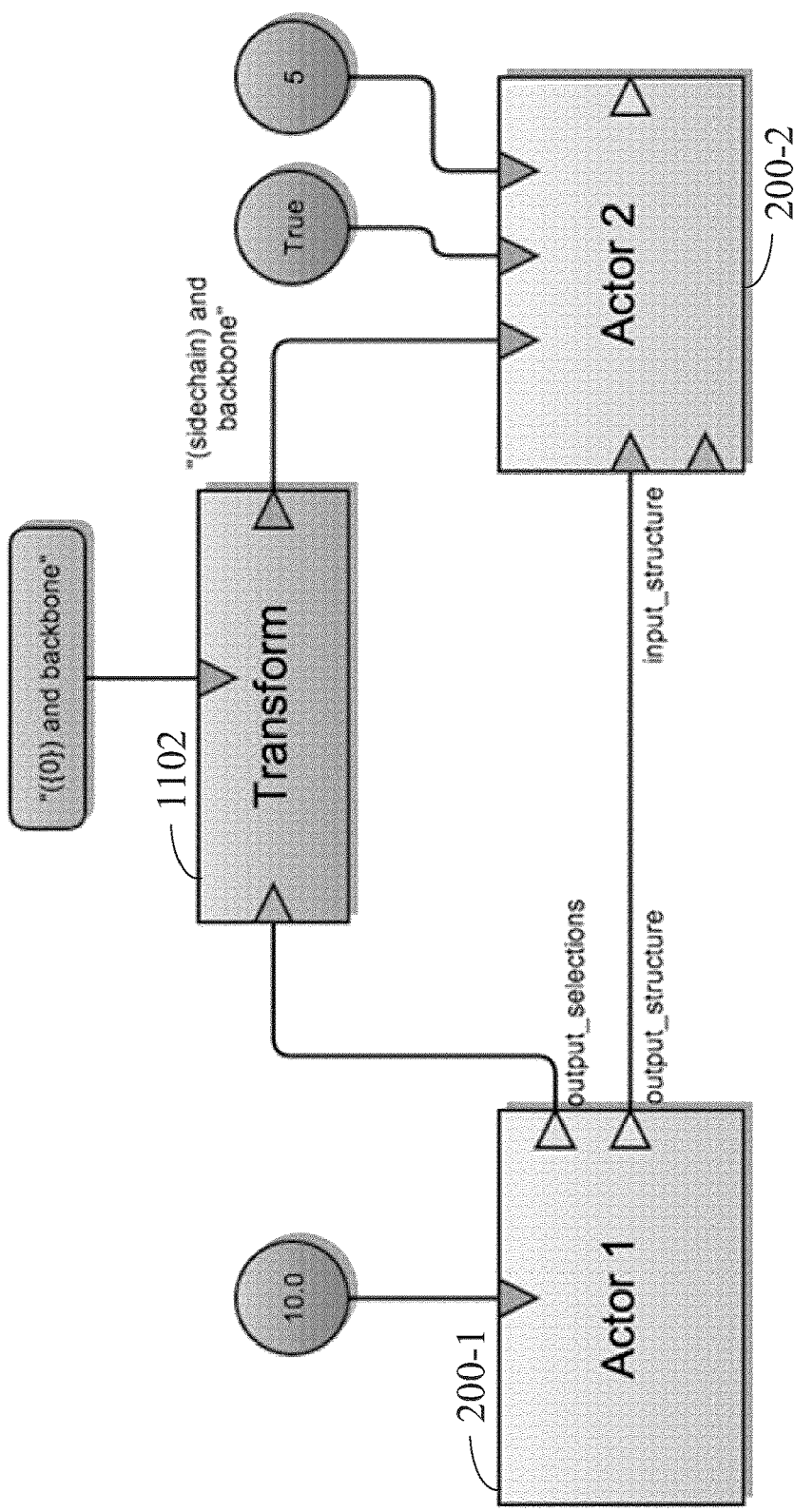
FIG. 11 illustrates the use of option ports in actors in a workflow, according to some embodiments.

Continuing to refer to FIG. 7, an actor class 202 further defines one or more option port classes 210. An option port is a basic port type that can receive a scalar value, e.g. an integer or a string. Option ports can also receive a transform. As illustrated in FIG. 11, a transform 1102 takes one or more outputs from a first actor as a parameter and reads the data from the outputs into a scalar. Within an actor 200, the option port will return a value, e.g: accessing "ports.selection" will return a string. For example:

```
class Foo(Actor):
    opt = Option("some option", IntType)
    def execute(self, ports):
        num = ports.opt # num = 5
    ## in the workflow init( )
    a = flow.add(Foo("actorA", opt=5))
```

Continuing to refer to FIG. 7, an actor class 202 further defines one or more tasks 212 that are performed by the actor. Examples of tasks 212 include, but are not limited to, molecular dynamics algorithms, structure refinement algorithms, homology modeling algorithms, calculation of accessible surface area term for a polymer, calculation of a potential energy term for a polymer, calculation of a solvent model for a polymer, calculation of a protein side-chain term for a polymer, calculation of a free volume term for a polymer, calculation of a packing efficiency term for a polymer (see e.g., Dahiyat et al., 1997, "Probing the role of packing specificity in protein design" PNAS 94:10172-10177, which is hereby incorporated by reference herein in its entirety), calculation of a number of interatomic contacts in a polymer (see e.g., Seeliger and L. de Groot, 2007, "Atomic contacts in protein structures. A detailed analysis of atomic radii, packing, and overlaps", Proteins-Structure Function and Bioinformatics 68:591-601, which is hereby incorporated by reference herein in its entirety), and a binding energy calculation for a polymer (see e.g., Gohlke et al., 2003, "Insights into protein-protein binding by binding free energy calculation and free energy decomposition for the Ras-Raf and Ras-RalGDS complexes", Journal of Molecular Biology 330:891-913, which is hereby incorporated by reference herein in its entirety).

Each actor 202 can specify what resources are required by the actor. For example, an actor can specify that completion of the actor takes a predetermined amount of CPU time (e.g., one hour) and requires a specified amount of random access memory (e.g. 500 megabytes of RAM memory); whereas another actor which is much more computationally intensive could specify that it requires 24 hours of CPU time to run and take 2 gigabytes of RAM memory. In such instances, the grid engine server module 44 will match these resource requirements against the resources of available computation servers so that each respective actor is run on a server that is capable of providing the resources required of the respective actor. As such, each actor 200 has two main functions that are coded. The first defines the input (via use of input port classes 204 and multi-input port classes 206), the output (output port classes 208) and the scientific options (option ports 210 and tasks 212). The second defines what the resources are needed in order to run the actor 200. In many instances, the resource requirements of an actor 200 are left blank. In such instances, the resource requirements of the actor 200 take on default requirement values. In many instances, this is sufficient. In instances where the resource requirements of an actor are extensive such that only a subset of the server nodes available to system 10 can perform the calculations specified by the actor, such resource designations are useful to prevent assignment of the actor to a server node that is incapable of accommodating the resource requirements of the actor. In some embodiments, the actor 200 can specify that the actor is to be run on a graphics processing unit (GPU) rather than a standard central processing unit (CPU). For instance, many molecular dynamics protocols run faster on GPU than a CPU. In this way, the grid engine server module 200 can direct all jobs related to molecular dynamics to run on nodes that have GPUs attached to them.

In some embodiments, the programs or modules identified above correspond to sets of instructions for performing a function described above. The sets of instructions can be executed by one or more processors (e.g., the CPUs 22). The above identified modules or programs (e.g., sets of instructions) need not be implemented as separate software programs, procedures or modules, and thus various subsets of these programs or modules may be combined or otherwise re-arranged in various embodiments. In some embodiments, memory 36 stores a subset of the modules and data structures identified above. Furthermore, memory 36 may store additional modules and data structures not described above.

In some embodiments, actors can be turned off or on dynamically within a workflow depending on the results of the preceding set of actors within the workflow. For example, in a workflow that involves running a computationally intensive algorithm on a structure, typically this should only be run if the preceding algorithm resulted in a low energy and favorable structure. Therefore typically in such a workflow, the preceding actor would compute the potential energy of the structure, and if that energy was below a user specific threshold, only then would the subsequent computationally intensive actor be run, otherwise that stage would be skipped. In other embodiments, the actor can be turned off for the entire workflow in a predetermined manner, for example by setting "enable=False" in the workflow configuration file. This is used in cases where the actor is either not computationally feasible to run at all, or in cases where it does not make scientific sense to run it for that particular instance of a workflow. An example could be an actor that computes the Quantum Mechanical (QM) energy of the system, which makes sense if the input to the workflow is an enzyme, but is not relevant if the input to the workflow is a protein antibody.

Figure 8:
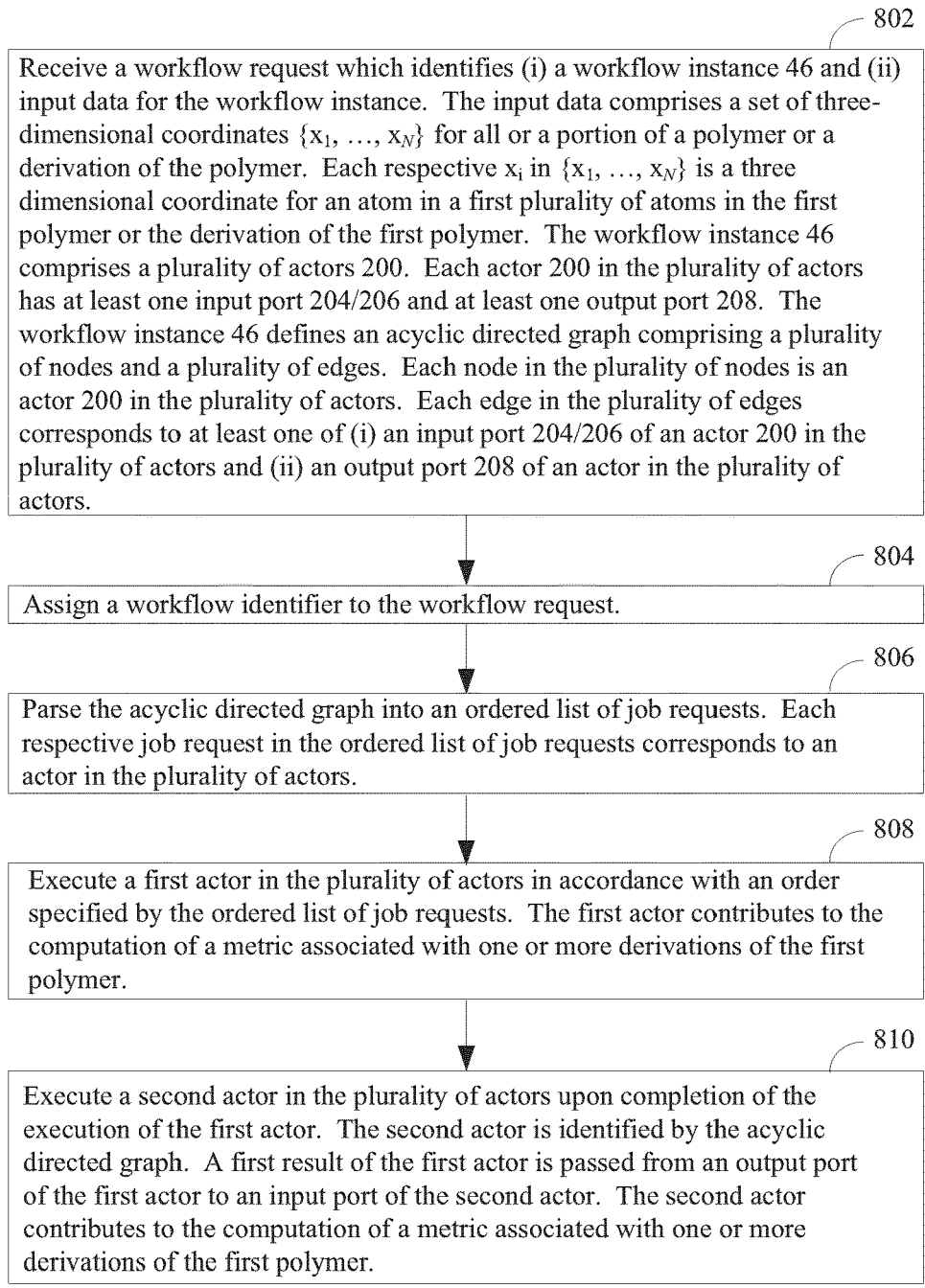
FIG. 8 illustrates a method of identifying an effect of one or more derivations of one or more polymers, according to some embodiments.

Now that a system in accordance with the systems and methods of the present disclosure has been described, attention turns to FIG. 8 which illustrates an exemplary method in accordance with the present disclosure.

Step 802. In step 802, a workflow request is received by a grid engine server module 44. In some embodiments, a workflow is submitted with a "submit" command. The work flow request identifies (i) a workflow instance 46 and (ii) input data for the workflow instance. In typical embodiments, this information is contained within a configuration file 68. In some embodiments, the configuration file is in human readable ASCII text format and contains information about which workflow to run and what parameters to run it with. The content of the configuration file depends on specific workflow but typically has a common [workflow] section which has a type option that specifies the workflow type. This value allows the workflow to be automatically converted into the directed graph of nodes and edges depending on the type of workflow, without additional user input. In some embodiments, the grid engine server module is used to parse and validate the values in the configuration file 68.

The following is an example of a configuration file 68 for a packing workflow:

```
pack workflow configuration excerpt
# pack workflow parameters
########################
# Workflow parameters
########################
[workflow]
# Type of workflow to run. (one of { '_test', 'equilibration',
'interface_repack', 'loop_modelling', 'loop_reconstruction', 'md',
'md_analysis', 'mean_field_pack', 'mean_field_packing', 'pack',
'residue_contacts' })
type = 'pack'
# Project name (string)
project = None
# Job priority. Between -1024 (lower) and 0 (higher) (integer)
priority = -500
###############################
# ZymePack workflow options
###############################
[pack]
# Enable the backrub/TAS stage (boolean)
backrub = True
###############
# input files
###############
[inputs]
# Input structure (existing file path)
structure = None
###########################
# ForceFieldDB parameters
###########################
[ffdb]
# Name of force field (string)
ffdb = 'amber'
# Name of rotamer lib (string)
rotlib = 'dunbrack'
# Use backbone-dependent rotamers (boolean)
rotlib_bbdep = False
```

In the example above, lines beginning with a # are comments, usually for the instructions that come immediately below them. A section of the configuration file is denoted by a name enclosed in square brackets, e.g: [ffdb]. An option is a name followed by an equal sign and a value. Every option in the configuration file has a data type which is indicated by the string in braces after the option description, e.g.: (float). The value assigned to the field below must match this type. Each type has a different syntax, for example, equivalent to that in the Python programming language. The following table shows an example of some of the types.

| Type | Example |
| --- | --- |
| string | 'this is a string' |
| integer | 42 |
| float | 47.5, requires at least one decimal place so use 42.0 instead of 42. |
| boolean | True or False |

The [workflow] section of the configuration file is common to all workflows. It sets a number of run-time parameters including, "type," "project" and "priority". "Type" means the type of workflow to run, e.g. "packing." The "project" is the name of the project associated with the workflow run. The "priority" is the priority with which the workflow is to be submitted (e.g., a number from −1024 to 0, with higher valued workflows being more likely to be scheduled first).

The input data used by a workflow instance 46 created for a workflow request comprises a set of three-dimensional coordinates $\{x_1, \ldots, x_N\}$ for all or a portion of a polymer or a derivation of the polymer. Each respective $x_i$ in $\{x_1, \ldots, x_N\}$ is a three dimensional coordinate for an atom in a first plurality of atoms in the first polymer or the derivation of the first polymer. In some embodiments the first polymer is a protein, a polypeptide, a polynucleic acid, a polyribonucleic acid, a polysaccharide, or an assembly of any combination thereof.

The workflow instance 46 comprises a plurality of actors. Each actor in the plurality of actors has at least one input port and at least one output port. The relationship between actor input ports and actor output ports in the plurality of actors defines an acyclic directed graph comprising a plurality of nodes and a plurality of edges.

An example of such an acyclic directed graph is provided in FIG. 3. Referring to FIG. 3, each node in the plurality of nodes of the acyclic directed graph 320 is an actor in the plurality of actors. Each edge in the plurality of edges corresponds to at least one of (i) an input port of an actor in the plurality of actors and (ii) an output port of an actor in the plurality of actors. Examples of edges between actors are illustrated in FIG. 4. However, it will be appreciated that an input port 204 of an actor 200 can be tied to a predetermined file path in addition to, or instead of the output port 208 of one or more other actors 200 in the workflow instance 46.

In typical embodiments, the polymer or the derivation of the polymer evaluated by a workflow comprises a set of $\{p_1, \ldots, p_K\}$ particles. Each particle $p_i$ in the set of $\{p_1, \ldots, p_K\}$ particles represents a different plurality of covalently bound atoms in the polymer. In one example, the polymer is a polynucleic acid and each particle $p_i$ in the set of $\{p_1, \ldots, p_K\}$ particles represents a nucleic acid residue in the polynucleic acid. In another example, the polymer is a polyribonucleic acid and each particle $p_i$ in the set of $\{p_1, \ldots, p_K\}$ particles represents a ribonucleic acid residue in the polyribonucleic acid. In still another example, the polymer is a polysaccharide and each particle $p_i$ in the set of $\{p_1, \ldots, p_K\}$ particles represents a monosaccharide unit or a disaccharide unit in the polysaccharide.

In still another example, the polymer is a protein and each particle $p_i$ in the set of $\{p_1, \ldots, p_K\}$ particles represents a residue in the protein. In some such embodiments, each respective coordinate $x_i$ in $\{x_1, \ldots, x_M\}$ is the three-dimensional coordinates of a corresponding atom in the polymer in three-dimensional space.

A polymer, such as those studied using the disclosed systems and methods, is a large molecule composed of repeating structural units. These repeating structural units are termed particles or residues interchangeably herein. In some embodiments, each particle $p_i$ in the set of $\{p_1, \ldots, p_K\}$ particles represents a single different residue in the polymer. To illustrate, consider the case where the polymer comprises 100 residues. In this instance, the set of $\{p_1, \ldots, p_K\}$ comprises 100 particles, with each particle in $\{p_1, \ldots, p_K\}$ representing a different one of the 100 particles.

In some embodiments, the polymer is a natural material. In some embodiments, the polymer is a synthetic material. In some embodiments, the polymer is an elastomer, shellac, amber, natural or synthetic rubber, cellulose, Bakelite, nylon, polystyrene, polyethylene, polypropylene, or polyacrylonitrile, polyethylene glycol, or polysaccharide.

In some embodiments, the polymer is a heteropolymer (copolymer). A copolymer is a polymer derived from two (or more) monomeric species, as opposed to a homopolymer where only one monomer is used. Copolymerization refers to methods used to chemically synthesize a copolymer. Examples of copolymers include, but are not limited to, ABS plastic, SBR, nitrile rubber, styrene-acrylonitrile, styrene-isoprene-styrene (SIS) and ethylene-vinyl acetate. Since a copolymer consists of at least two types of constituent units (also structural units, or particles), copolymers can be classified based on how these units are arranged along the chain. These include alternating copolymers with regular alternating A and B units. See, for example, Jenkins, 1996, "Glossary of Basic Terms in Polymer Science," Pure Appl. Chem. 68 (12): 2287-2311, which is hereby incorporated herein by reference in its entirety. Additional examples of copolymers are periodic copolymers with A and B units arranged in a repeating sequence (e.g. $(A\text{-}B\text{-}A\text{-}B\text{-}B\text{-}A\text{-}A\text{-}A\text{-}A\text{-}B\text{-}B\text{-}B)_n$). Additional examples of copolymers are statistical copolymers in which the sequence of monomer residues in the copolymer follows a statistical rule. If the probability of finding a given type monomer residue at a particular point in the chain is equal to the mole fraction of that monomer residue in the chain, then the polymer may be referred to as a truly random copolymer. See, for example, Painter, 1997, *Fundamentals of Polymer Science*, CRC Press, 1997, p 14, which is hereby incorporated by reference herein in its entirety. Still other examples of copolymers that may be evaluated using the disclosed systems and methods are block copolymers comprising two or more homopolymer subunits linked by covalent bonds. The union of the homopolymer subunits may require an intermediate non-repeating subunit, known as a junction block. Block copolymers with two or three distinct blocks are called diblock copolymers and triblock copolymers, respectively.

In some embodiments, the native polymer is in fact a plurality of polymers, where the respective polymers in the plurality of polymers do not all have the molecular weight. In such embodiments, the polymers in the plurality of polymers fall into a weight range with a corresponding distribution of chain lengths. In some embodiments, the native polymer is a branched polymer molecule comprising a main chain with one or more substituent side chains or branches. Types of branched polymers include, but are not limited to, star polymers, comb polymers, brush polymers, dendronized polymers, ladders, and dendrimers. See, for example, Rubinstein et al., 2003, *Polymer physics*, Oxford; New York: Oxford University Press. p. 6, which is hereby incorporated by reference herein in its entirety.

In some embodiments, the native polymer is a polypeptide. As used herein, the term "polypeptide" means two or more amino acids or residues linked by a peptide bond. The terms "polypeptide" and "protein" are used interchangeably herein and include oligopeptides and peptides. An "amino acid," "residue" or "peptide" refers to any of the twenty standard structural units of proteins as known in the art, which include imino acids, such as proline and hydroxyproline. The designation of an amino acid isomer may include D, L, R and S. The definition of amino acid includes nonnatural amino acids. Thus, selenocysteine, pyrrolysine, lanthionine, 2-aminoisobutyric acid, gamma-aminobutyric acid, dehydroalanine, ornithine, citrulline and homocysteine are all considered amino acids. Other variants or analogs of the amino acids are known in the art. Thus, a polypeptide may include synthetic peptidomimetic structures such as peptoids. See Simon et al., 1992, Proceedings of the National Academy of Sciences USA, 89, 9367, which is hereby incorporated by reference herein in its entirety. See also Chin et al., 2003, Science 301, 964; and Chin et al., 2003, Chemistry & Biology 10, 511, each of which is incorporated by reference herein in its entirety.

The polymers that are polypeptides and that are evaluated in accordance with some embodiments of the disclosed systems and methods may also have any number of post-translational modifications. Thus, in such polypeptides includes those that are modified by acylation, alkylation, amidation, biotinylation, formylation, γ-carboxylation, glutamylation, glycosylation, glycylation, hydroxylation, iodination, isoprenylation, lipoylation, cofactor addition (for example, of a heme, flavin, metal, etc.), addition of nucleosides and their derivatives, oxidation, reduction, pegylation, phosphatidylinositol addition, phosphopantetheinylation, phosphorylation, pyroglutamate formation, racemization, addition of amino acids by tRNA (for example, arginylation), sulfation, selenoylation, ISGylation, SUMOylation, ubiquitination, chemical modifications (for example, citrullination and deamidation), and treatment with other enzymes (for example, proteases, phosphotases and kinases). Other types of posttranslational modifications are known in the art and are also included.

In some embodiments, a polymer evaluated using the disclosed systems and methods is an organometallic compound. An organometallic compound is chemical compound containing bonds between carbon and metal. In some instances, organometallic compound is distinguished by the prefix "organo-" e.g. organopalladium compounds. Examples of such organometallic compounds include all Gilman reagents, which contain lithium and copper. Tetracarbonyl nickel, and ferrocene are examples of organometallic compounds containing transition metals. Other examples include organomagnesium compounds like iodo(methyl)magnesium MeMgI, diethylmagnesium ($Et_2Mg$), and all Grignard reagents; organolithium compounds such as n-butyllithium (n-BuLi), organozinc compounds such as diethylzinc ($Et_2Zn$) and chloro(ethoxycarbonylmethyl)zinc ($ClZ_nCH_2C(=O)OEt$); and organocopper compounds such as lithium dimethylcuprate ($Li^+[CuMe_2]^-$). In addition to the traditional metals, lanthanides, actinides, and semimetals, elements such as boron, silicon, arsenic, and selenium are considered form organometallic compounds, e.g. organoborane compounds such as triethylborane ($Et_3B$).

In some embodiments, a polymer studied using the systems and methods of the present disclosure is a surfactant. Surfactants are compounds that lower the surface tension of a liquid, the interfacial tension between two liquids, or that between a liquid and a solid. Surfactants may act as detergents, wetting agents, emulsifiers, foaming agents, and dispersants. Surfactants are usually organic compounds that are amphiphilic, meaning they contain both hydrophobic groups (their tails) and hydrophilic groups (their heads). Therefore, a surfactant molecule contains both a water insoluble (or oil soluble) component and a water soluble component. Surfactant molecules will diffuse in water and adsorb at interfaces between air and water or at the interface between oil and water, in the case where water is mixed with oil. The insoluble hydrophobic group may extend out of the bulk water phase, into the air or into the oil phase, while the water soluble head group remains in the water phase. This alignment of surfactant molecules at the surface modifies the surface properties of water at the water/air or water/oil interface.

Examples of ionic surfactants include ionic surfactants such as anionic, cationic, or zwitterionic (ampoteric) surfactants. Anionic surfactants include (i) sulfates such as alkyl sulfates (e.g., ammonium lauryl sulfate, sodium lauryl sulfate), alkyl ether sulfates (e.g., sodium laureth sulfate, sodium myreth sulfate), (ii) sulfonates such as docusates (e.g., dioctyl sodium sulfosuccinate), sulfonate fluorosurfactants (e.g., perfluorooctanesulfonate and perfluorobutanesulfonate), and alkyl benzene sulfonates, (iii) phosphates such as alkyl aryl ether phosphate and alkyl ether phosphate, and (iv) carboxylates such as alkyl carboxylates (e.g., fatty acid salts (soaps) and sodium stearate), sodium lauroyl sarcosinate, and carboxylate fluorosurfactants (e.g., perfluorononanoate, perfluorooctanoate, etc.). Cationic surfactants include pH-dependent primary, secondary, or tertiary amines and permanently charged quaternary ammonium cations. Examples of quaternary ammonium cations include alkyltrimethylammonium salts (e.g., cetyl trimethylammonium bromide, cetyl trimethylammonium chloride), cetylpyridinium chloride (CPC), benzalkonium chloride (BAC), benzethonium chloride (BZT), 5-bromo-5-nitro-1,3-dioxane, dimethyldioctadecylammonium chloride, and dioctadecyldimethylammonium bromide (DODAB). Zwitterionic surfactants include sulfonates such as CHAPS (3-[(3-Cholamidopropyl)dimethylammonio]-1-propanesulfonate) and sultaines such as cocamidopropyl hydroxysultaine. Zwitterionic surfactants also include carboxylates and phosphates.

Nonionic surfactants include, but are not limited to, fatty alcohols such as cetyl alcohol, stearyl alcohol, cetostearyl alcohol, and oleyl alcohol. Nonionic surfactants also include polyoxyethylene glycol alkyl ethers (e.g., octaethylene glycol monododecyl ether, pentaethylene glycol monododecyl ether), polyoxypropylene glycol alkyl ethers, glucoside alkyl ethers (decyl glucoside, lauryl glucoside, octyl glucoside, etc.), polyoxyethylene glycol octylphenol ethers ($C_8H_{17}$—($C_6H_4$)—(O—$C_2H_4$)$_{1-25}$—OH), polyoxyethylene glycol alkylphenol ethers ($C_9H_{19}$—($C_6H_4$)—(O—$C_2H_4$)$_{1-25}$—OH, glycerol alkyl esters (e.g., glyceryl laurate), polyoxyethylene glycol sorbitan alkyl esters, sorbitan alkyl esters, cocamide MEA, cocamide DEA, dodecyldimethylamine oxideblock copolymers of polyethylene glycol and polypropylene glycol (poloxamers), and polyethoxylated tallow amine. In some embodiments, a polymer studied using the disclosed systems and methods is a reverse micelle, or liposome.

In some embodiments, a polymer studied using the disclosed systems and methods is a fullerene. A fullerene is any molecule composed entirely of carbon, in the form of a hollow sphere, ellipsoid or tube. Spherical fullerenes are also called buckyballs, and they resemble the balls used in association football. Cylindrical ones are called carbon nanotubes or buckytubes. Fullerenes are similar in structure to graphite, which is composed of stacked graphene sheets of linked hexagonal rings; but they may also contain pentagonal (or sometimes heptagonal) rings.

In some embodiments, the set of three-dimensional coordinates $\{x_1, \ldots, x_M\}$ for the polymer inputted into a workflow instance 46 are obtained by x-ray crystallography, nuclear magnetic resonance spectroscopic techniques, or electron microscopy. In some embodiments, the set of three-dimensional coordinates $\{x_1, \ldots, x_M\}$ is obtained by modeling (e.g., molecular dynamics simulations).

In some embodiments, polymer evaluated by a workflow instance 46 includes two different types of polymers, such as a nucleic acid bound to a polypeptide. In some embodiments, a polymer evaluated by a workflow instance 46 includes two polypeptides bound to each other. In some embodiments, such a polymer includes one or more metal ions (e.g. a metalloproteinase with a one or more zinc atoms) and/or is bound to one or more organic small molecules (e.g., an inhibitor). In such instances, the metal ions and or the organic small molecules may be represented as one or more additional particles $p_i$ in the set of $\{p_1, \ldots, p_K\}$ particles representing the polymer.

In some embodiments, there are ten or more, twenty or more, thirty or more, fifty or more, one hundred or more, between one hundred and one thousand, or less than 500 particles in a polymer evaluated using a workflow instance 46 of the present disclosure.

There is no requirement that each atom in a particle $p_i$ be covalently bound to each other atom in a particle in a polymer evaluated in a workflow instance 46 of the present disclosure. More typically, each atom in a particle $p_i$ is covalently bound to at least one other atom in the particle, as is the typical case in an amino acid residue in a polypeptide. Moreover, typically, for each respective particle $p_i$ in the set of $\{p_1, \ldots, p_K\}$ particles, there is at least one atom in the respective particle $p_i$ that is covalently bound to an atom in another particle in the set of $\{p_1, \ldots, p_K\}$ particles.

In addition to polymer data, input data to a workflow may include data such as a rotamer library. Rotamers are usually defined as low energy side chain conformations. The use of an optional side chain rotamer library allows for the sampling of the most likely side chain conformations by an actor, saving time and producing structures that are more likely to have lower energy. See, for example, Shapovalov and Dunbrack, 2011, "A smoothed backbone-dependent rotamer library for proteins derived from adaptive kernel density estimates and regressions," Structure 19, 844-858; and Dunbrack and Karplus, 1993, "Backbone-dependent rotamer library for proteins. Application to side chain prediction", J. Mol. Biol. 230: 543-574, each of which is hereby incorporated by reference herein in its entirety. In some embodiments dead end elimination principals are used by actors to reject certain conformations. For instance, in some embodiments, a first rotamer for a given side chain of a residue in a polymer is eliminated if any alternative rotamer for the given side chain of the residue in the polymer contributes less to the total energy of the polymer than the first rotamer. In some embodiments, this form of dead end elimination principle is used in addition to a Monte Carlo based simulated annealing process to select rotamers for use. Dead end elimination principles are disclosed in Desmet et al., 1992, "The dead-end elimination theorem and its use in protein side-chain position", Nature 356: 539-542; Goldstein, 1994, "Efficient rotamer elimination applied to protein side chains and related spin glasses", Biophys. J. 66: 1335-1340; and Lasters et al., 1995, "Enhanced dead-end elimination in the search for the global minimum energy conformation of a collection of protein side chains", Protein Eng. 8: 815-822; and Leach and Lemon, 1998, "Exploring the Conformational Space of Protein Side Chains Using Dead-End Elimination and the A* Algorithm", Proteins: Structure, Function, and Genetics 33: 227-239 (1998), each of which is hereby incorporated by reference in its entirety.

In addition to polymer data, input data to a workflow may specify an atomic force field, such as the MSI CHARMM force field, variants thereof, and equivalents thereof. See Brooks, 1983, J. Comp. Chem., 4, 187-217, and Schleyer, 1998, CHARMM: The Energy Function and Its Parameterization with an Overview of the Program, in The Encyclopedia of Computational Chemistry, 1:271-277 eds., John Wiley & Sons, Chichester, each of which is hereby incorporated by reference.

Step 804. In step 804, the grid engine server module 44 assigns a workflow identifier 50 to the workflow instance 46 created in response to the workflow request received in step 802. This workflow identifier 50 is an optional identifier that is used to keep track of the various actors associated with the workflow instance 46 as well as the data generated by such actors. As illustrated in FIG. 1, in typical instances, at any given time, grid engine server module 44 services more than one workflow instance 46. For instance, in some embodiments, at any given time, in some instances, grid engine server module 44 services more than two, three, four, five, six, seven, eight, nine, or ten workflow instances 46 at the same time. In some embodiments, at any given time, grid engine server module 44 services more than ten, twenty, thirty, forty, fifty, sixty, seventy, eighty, or ninety workflow instances 46 at the same time.

Step 806. In step 806, the acyclic directed graph 48 that is defined by the logic of the input and output ports of the respective actors is parsed into an ordered list of job requests. For example, referring to acyclic directed graph 320 of FIG. 3, fulfillment of graph 320 requires a job request for actors 200-1-1, 200-1-2, 200-1-3, 200-1-4, and 200-1-5. Because the output of actor 200-1-1 is used as the input to actors 200-1-2 and 200-1-3, the ordered list of job requests begins with a job request for actor 200-1-1, followed by job requests for actors 200-1-2 and 200-1-3. Each job request specifies the identity of an actor to be run. To complete servicing of graph 320, a job request for actor 200-1-4, to be run after the job request for actor 200-1-3, and a job request for actor 200-105, to be run after the job request for actor 200-1-4, are each needed. It will be appreciated that, for some graphs, there is more than one order of the job requests that can be used. For instance, graph 320 can be serviced by job requests in the order {200-1-1, 200-1-2, 200-1-3, 200-1-4, and 200-1-5} or {200-1-1, 200-1-3, 200-1-4, 200-1-5, and 200-1-2}. A criterion in determining the order of job requests is to ensure that a job request for an actor that requires input from other actors be listed after the job requests for these other actors.

A job request is created for each actor based on its required resources and execution strategy. The jobs are put into a hold state to prevent any of them from executing before all job submissions for a workflow have been completed. This process is repeated for each action, with the request for subsequent actions being updated with job dependencies for the actions required to precede it. Finally, after all the jobs have been submitted, a client that is originating the workflow request sends a request to the grid engine server module 44 to release the holds on the jobs. The workflow begins executing at this point.

Figure 9:
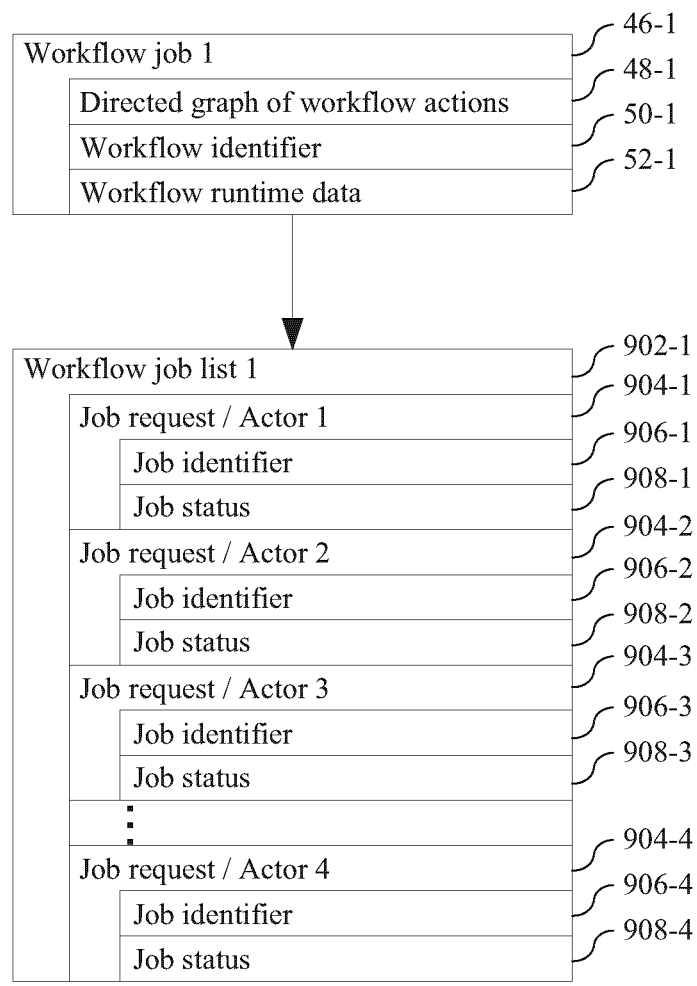
FIG. 9 illustrates how an acyclic directed graph of a workflow is converted to a workflow job list, according to some embodiments.

FIG. 9 summarizes the data structure transformation that arises as the result of the process set forth in step 806. A workflow job 46 that corresponds to a workflow 66 includes a plurality of actors 200. The input ports 204, multi-input ports 206, and output ports 208 of the workflow job request 902 define a directed graph of workflow actions 48 for the workflow. Further, there is a workflow identifier 50 for the workflow and associated workflow runtime data 52. Upon execution of step 806, the acyclic directed graph 48 is parsed into an ordered list of job requests 902. Each respective job request 904 in the ordered list of job requests corresponds to an actor in the plurality of actors. In some embodiments, each respective job request includes a job identifier 906 and a job status 908. When the workflow is executed, the grid engine server module 44 executes the job requests specified in the workflow job list 902.

Step 808. In step 808, a first actor in the plurality of actors for a workflow request is executed in accordance with an order specified by the ordered list of job requests that was derived in step 806. In practice, in typical embodiments, the first job request 904 in the workflow job list for the workflow request is executed. This first job request corresponds to the first actor. Execution of the first actor contributes to the computation of a metric associated with one or more derivations of the first polymer. Advantageously, some embodiments of the disclosed systems and methods provide several ways to control running and completed workflows using specific commands.

For instance, the "from" command is used to run additional workflow related commands that depend on the type of workflow. The command provides additional post-flow functionality such as generating metrics tables, pymol sessions, or other outputs. In some embodiments, the list of available commands for a workflow can be obtained for a workflow by running the "from" command without any additional arguments. The following is an exemplary execution of the "from" command:

zymeflow from {workflow directory}.

To get help on the options of a command, the following can be used in some embodiments:

zymeflow from {workflow directory} {workflow command} --help

A specific command can be executed as follows in some embodiments:

--- zymeflow from {workflow directory} {workflow command} {workflow command arguments}

---

In one example for a packing workflow, it is possible to produce a metrics table using the following command:

zymeflow from packing.flow metrics_table --out-csv table.csv

Another specific command is the "fromall" command. The "fromall" command works on the same principle as the "from" command. The primary difference being that "fromall" operates on a list of workflows as opposed to a single workflow. This allows the grid engine server module 44 to provide commands that aggregate data from multiple workflows. The general usage of the "fromall" command is:

--- zymeflow fromall {workflow1} {workflow2} {...} {workflow command} {workflow command arguments}

---

The above-identified commands require that all the workflows operated on by a command be of the same type. A list of available fromall commands can be obtained by running it on a single workflow without additional arguments as follows:

zymeflow fromall {workflow1}

To get help on the options of a command the following can be used in some embodiments:

zymeflow fromall {workflow1} {workflow command} --help

For instance, for a set of packing workflows, it is possible to generate a Pymol session of all their mutations using the following command:

zymeflow fromall packing1.flow packing2.flow single_pymol_session --align-on backbone --out-session session1.pymol Another specific command is the "halt" command. In some embodiments, the command:

zymeflow halt {workflow directory} will remove all jobs related to a workflow from the grid engine server module 44.

In some embodiments, the "hold" command zymeflow hold {workflow directory} temporarily suspends the execution of a workflow. The workflow's jobs will remain submitted to the cluster but will not attempt to run:

In some embodiments, the "info" command:

zymeflow info {workflow directory} provides some general information about a running workflow.

In some embodiments, the "inspect" command:

zymeflow inspect {workflow directory} backrub is used to get diagnostic information about an action in a running flow. If a specific task identifier is provided, the log files from that task are sent to the standard input output device:

zymeflow inspect {workflow directory} backrub 25.

In some embodiments, a "monitor" command is provided having three modes which provide for three different levels of detail. The most basic form of monitor is:

zymeflow monitor which provides an overview of the status of running workflows associated with a given user. A user can see a status of all workflows on the cluster by adding the --user='*' option:

zymeflow monitor --user='*'

Alternatively, a user can see the status of another user's workflows by adding the --user='someone' option:

zymeflow monitor --user='kamil'

The second monitor mode allows a user to monitor the status of a particular workflow:

zymeflow monitor {workflow directory} or by the given user identifier for a workflow:

zymeflow monitor uuid://4ab3c914-909c-11e1-94bb-00145e5533ec

By default this monitor mode only shows the status of actions which are currently running, waiting to be run, or in an error state for the workflow associated with the designated workflow. To include counts of completed tasks an --all-tasks option can be used.

It will take a moment for the grid engine server module 44 to check the job status information in several places, and return a single table showing how many tasks are in each state. In some embodiments, the possible states are as set forth in Table 1 below.

TABLE 1

Possible states for each job

| State | Description |
| --- | --- |
| Running | The task is currently running on the cluster |
| Error | The task has failed |
| Waiting | The task is ready to run, but is waiting for the cluster scheduler to assign it to a node |
| Held | The task cannot run because it is dependent on a job that has not completed successfully |

If the --all-tasks option is used the monitor command queries the job database to get information completed tasks and shows additional information regarding whether the task has successfully completed with no errors or whether a determination could not be made regarding the state of the task (likely because it is currently transitioning from one state to another).

The third mode of "monitor"

zymeflow monitor {workflow directory} {action name} shows the detailed status of an action's tasks. This can be used to determine which tasks are in an error state so they can be inspected for errors using inspect. Completed tasks are not shown by default but can be enabled with the "--all-tasks" option.

Advantageously, in some embodiments, using a prioritize command such as:

zymeflow prioritize {workflow directory} -600 allows the job priority of an entire workflow to be changed either before or after submission. In some embodiments, priority values are in the range −1023 to 1024, with larger positive numbers associated with those jobs that are more likely to be run first.

In some embodiments, the "release" command, such as:

zymeflow release {workflow directory} releases all jobs in a workflow after previously holding them with hold.

In some embodiments, the "show" command, such as:

zymeflow show {workflow directory} show provides a graphical representation of the target workflow. In some embodiments, when the "-dot" flag is used, the graph is printed to standard output in Graphviz dot syntax.

In some embodiments, the "submit" command, such as:

zymeflow submit {workflow directory} {parameters file} is used to submit a workflow run. In an exemplary convention, the specified workflow directory name ends in ".flow" and does not exist prior to execution of the "submit" command. In such conventions, the submit command creates the directory.

The parameters file can be generated via the template command. In some embodiments it may take a few minutes for the grid engine server module 44 to compute all of the job dependencies associated with a workflow 66. Advantageously, once the workflow has been submitted, workflow progress can be tracked using the "monitor" command.

Templates for workflows are generated using this command:

zymeflow template {workflow type}

By default the template is printed to the screen. The shell can be used to redirect the template to a file:

zymeflow template packing>packing.cfg

The values in the template can be pre-populated from another template using the --config flag:

zymeflow template packing --config packing_defaults defaults.cfg>packing.cfg

However, the type of workflow in the defaults must match that of the one being generated.

In some embodiments, all or a subset of the above commands can either be run on the command line of a particular operating system, or via a web interface by selecting a particular workflow from a list of available workflows, and clicking specific user interface elements to get additional information about that workflow. For example, an "Info" button is typically used to provide more information about that workflow, replacing the "zymeflow info < >" command described in the preceding paragraph.

Examples of tasks that the first actor may perform in step 808 include any of the tasks described above, including, for example, molecular dynamics algorithms, structure refinement algorithms, homology modeling algorithms, calculation of accessible surface area term for a polymer, calculation of a potential energy term for a polymer, calculation of a solvent model for a polymer, calculation of a protein side-chain term for a polymer, calculation of a free volume term for a polymer, calculation of a packing efficiency term for a polymer, calculation of a number of interatomic contacts in a polymer, and binding energy calculation for a polymer.

The following provides a specific example in which an input polymer is first modified, and then various physical parameters of the modified polymer are tested by an actor. While this example is subscribed to a single actor, it will be appreciated that the present disclosure is not so limiting and that any number of actors, in the form of a workflow, can be used to accomplish the teachings of this example. In the example, an actor uses a set of three-dimensional coordinates $\{x_1, \ldots, x_N\}$ for all or a portion of a polymer that was obtained as part of the input data described above in step 802. The actor further derives the polymer, in silico, by incorporating an atomic replacement, insertion or deletion to obtain the coordinates $\{y_1, \ldots, y_M\}$. In some embodiments, the polymer is a protein and the atomic replacement, insertion or deletion is a mutation of one or more residues in the polymer relative to the starting polymer in the input data. In some embodiments, the polymer in the input data is a protein and the derivation of the polymer differs from the native polymer by the insertion or deletion of one or more residues at one or more locations in the polymer. Typically, the N three-dimensional coordinates $\{x_1, \ldots, x_N\}$ for the input polymer and the set of M three-dimensional coordinates $\{y_1, \ldots, y_M\}$ for the derived polymer are already structurally refined. In some embodiments either the native or the derived set of coordinates, or both, are refined against a cost function with one or more exit conditions.

In some embodiments, a region of the polymer that encompasses the site of the atomic replacement, insertion or deletion is refined by the actor while all other portions of the polymer are held fixed. In some embodiments, the region of the polymer that encompasses the site of the atomic replacement, insertion or deletion consists of the atoms of the polymer that are within a threshold distance of the atomic replacement, insertion or deletion. In some embodiments, the distance threshold is "X" Angstroms, where "X" is any value between 5 and 50 (e.g., 5, 10, 15, 20, 25, 30, 35, 40, 45, 50, etc.).

By way of an example, consider a polymer in the input data that is a one hundred residue protein with a leucine at residue position 50. The atomic replacement is the replacement of this leucine with a phenylalanine, and those atoms in $\{y_1, \ldots, y_M\}$ that are within ten Angstroms of the $C_{alpha}$ carbon of phenylalanine 50 are selected for refinement by minimization module 54 while all other atoms of the derivation of the polymer are held fixed.

By way of another example, the polymer in the input data is a one hundred residue protein with a leucine at residue position 50, the atomic replacement is the replacement of this leucine with a phenylalanine, and those atoms in $\{x_1, \ldots, x_N\}$ that are in a residue that has at least one atom within ten Angstroms of the $C_{alpha}$ carbon of phenylalanine 50 are selected for refinement by the actor while other atoms of the derivation of the polymer are held fixed.

By way of still another example, the polymer in the input data is a one hundred residue protein with a leucine at residue position 50 and a proline at position 60, the atomic replacement is the replacement of the leucine at position 50 with a phenylalanine and the replacement of proline at position 60 with an alanine, and those atoms in $\{x_1, \ldots, x_N\}$ that are within ten Angstroms of the $C_{alpha}$ carbon of phenylalanine 50 or the $C_{alpha}$ carbon of alanine 60 are selected for refinement by minimization module 54 while all other atoms of the derivation of the polymer are held fixed.

By way of yet another example, the polymer in the input data is a one hundred residue protein with a leucine at residue position 50 and a proline at position 60, the atomic replacement is the replacement of the leucine at position 60 with a phenylalanine and the replacement of the proline at position 60 with an alanine, and those atoms in $\{x_1, \ldots, x_N\}$ that are in a residue that has at least one atom within ten Angstroms of the $C_{alpha}$ carbon of phenylalanine 50 or the $C_{alpha}$ carbon of alanine 60 are selected for refinement by the actor while other atoms of the derivation of the polymer are held fixed.

The above examples make it clear that, to modify the polymer in the input data, a residue of the native polymer is identified, in silico, and is optionally replaced with a different residue. In fact, more than one residue can be identified by an actor. In practice, one or more residues of the input polymer can be identified in the initial structural coordinates $\{x_1, \ldots, x_N\}$. In some embodiments, the identified one or more residues are either replaced with different residues or deleted. In some embodiments, one or more residues in the polymer in the input data are deleted when forming the derivation of the polymer in silico. In some embodiments, any combination of atomic replacement, insertion or deletion of atoms, including whole residues, into the native polymer is performed in order to arrive at the derivation of the polymer.

In one embodiment, a single residue of the input polymer is identified and replaced with a different residue, and the region of the derivation of the polymer that is selected for refinement is defined as a sphere having a predetermined radius, where the sphere is centered either on a particular atom of the mutated residue (e.g., $C_\alpha$ carbon in the case of proteins) or the center of mass of the identified residue. In some embodiments, the predetermined radius is five Angstroms or more, 10 Angstroms or more, or 20 Angstroms or more. For example, in one embodiment, the polymer in the input data is a protein comprising 200 residues and an alanine at position 100 (i.e., the $100^{th}$ residues of the 200 residue protein) that is found in the polymer 44 is changed to a tyrosine (i.e., A100W). Then, the region of the derivation of the polymer that is selected for refinement is defined based on the position of A100W. In some embodiments, the region of the polymer is the $C_{alpha}$ carbon or a designated main chain atom of residue 100 either before or after the side chain has been replaced.

In some embodiments, more than two residues are identified and the region of the polymer that is refined, in fact, is more than two regions. For example, in some embodiments, the polymer in the input data is a protein, two different residues are mutated, and the region of the derivation of the polymer that is refined comprises (i) a first sphere having a predetermined radius that is centered on the $C_{alpha}$ carbon of the first mutated residue and (ii) a second sphere having a predetermined radius that is centered on the $C_{alpha}$ carbon of the second mutated residue. Depending on how close the two substitutions are, the residues may or may not overlap. In alternative embodiments, more than two residues are identified, and optionally mutated, and the region that is selected for refinement is a single contiguous region.

In some embodiment, two, three, four, five, or more than five residues of the polymer in the input data are mutated in silico by an actor to form a derivation of the polymer that is then further studied. In some embodiments, this plurality of residues consists of three residues. There is no requirement that these residues be contiguous within the native polymer. In some of the foregoing embodiments, the region of the derivation of the polymer containing mutations relative to the polymer in the input data is a single region that is defined as a sphere having a predetermined radius, where the sphere is centered at a center of mass of the plurality of identified residues either before or after optional substitution. In some embodiments, the predetermined radius is five Angstroms or more, 10 Angstroms or more, or 20 Angstroms or more. For example, in one embodiment, the native polymer is a protein comprising 200 residues and an alanine at position 100 (i.e., the $100^{th}$ residue of the 200 residue protein) that is found in the native polymer is changed to a tyrosine (i.e., A100W) and a leucine at position 102 of the native polymer is changed to an isoleucine (i.e., L102I) in order to form the derivation of the polymer in silico. Then, the region of the derivation of the polymer 49 is defined based on the positions of A100W and L102I. In some embodiments, the region of the derivation of the polymer is the center of mass of A100W and L102I either before or after the mutations have been made. It will be appreciated that this center of mass may fall outside the Van der Waals space occupied by residues 100 and 102.

Now that there has been discussion of what regions of the polymers are refined in the example, exemplary refinement protocols are provided. In these examples, the one or more regions of a polymer selected for refinement are represented by the cost function in an actor. In some embodiments, the cost function estimates the potential energy of the selected portions of the input polymer (when refining the selected portions of the input polymer) or the selected portions of the derivation of the polymer (when refining the selected portions of the derivation of the polymer). In such embodiments, the cost function includes terms relating to the various relationships between the parts of the polymer. Thus, in some embodiments, the cost function includes terms that account for energy due to, for example, bond length, bond angle, and dihedral angles, as well as nonbonding interactions such as Coulombic and Lennard-Jones interactions within the polymer being refined. In some embodiments, the cost function further includes cross or other higher order terms.

In some embodiments, the cost function is minimized using a quasi-Newton method, such as the Broyden-Fletcher-Goldfarb-Shanno (BFGS). In quasi-Newton methods, the Hessian matrix of second derivatives need not be evaluated directly. Instead, the Hessian matrix is approximated using rank-one updates specified by gradient evaluations (or approximate gradient evaluations). Quasi-Newton methods are a generalization of the secant method to find the root of the first derivative for multidimensional problems. In multi-dimensions the secant equation does not specify a unique solution, and quasi-Newton methods differ in how they constrain the solution.

In some embodiments, the cost function is minimized using a random walk method, such as simulated annealing ("SA"), that does not require derivatives. In some such embodiments, a "hill-climbing method", such as steepest decent or BFGS, is used. In some embodiments, simulated annealing is used to refine the cost function 56 rather than hill-climbing methods.

As noted above, the cost function is minimized until an exit condition is achieved. In some instances, the exit condition is determined by the method by which the cost function is minimized. For example, Berinde, 1997, Novi SAD J. Math, 27, 19-26, which is incorporated herein by reference, outlines some exit conditions for Newton's method. In some embodiments, the exit condition is achieved when a predetermined maximum number of iterations of the refinement algorithm used to refine the cost function have been computed. In some embodiments, the predetermined maximum number of iterations is ten iterations, twenty iterations, one hundred iterations or one thousand iterations.

In some embodiments the selected regions of the native polymer or the derivation of the polymer are refined using a minimization algorithm and a suitable force field, such as the MSI CHARMM force field, variants thereof, and equivalents thereof. See Brooks, 1983, J. Comp. Chem., 4, 187-217, and Schleyer, 1998, CHARMM: The Energy Function and Its Parameterization with an Overview of the Program, in The Encyclopedia of Computational Chemistry, 1:271-277 eds., John Wiley & Sons, Chichester, each of which is hereby incorporated by reference.

At this stage, the coordinates for a polymer in the input data and the coordinates for a derivation of this polymer have been obtained. The polymer in the input data and the derivation of the polymer differ from each other by some combination of atomic replacements, insertions, or deletions, or any combination thereof, as described above. Furthermore, at least some of the coordinates of both the polymer in the input data and the derivation of the polymer have been refined as described above. It will be appreciated that there is no requirement that the polymer in the input data correspond to, or be, a naturally occurring polymer. The partial refinement of the polymer in the input data and the partial refinement of the derivation of the polymer allows for the computation of the affect, such as a thermodynamic affect (e.g., entropy, average energy, average enthalpy, free energy or heat capacity) of the derivation on the polymer using techniques such as those disclosed in U.S. patent application Ser. No. 61/793,203, filed Mar. 15, 2013, which is hereby incorporated by reference herein in its entirety.

Step 810. In step 810, a second actor in the plurality of actors associated with a workflow 66 is executed upon completion of the execution of the first actor. The second actor is identified by the acyclic directed graph defined by the input ports and the export ports of the plurality of actors associated with the workflow. A first result of the first actor is passed from an output port of the first actor to an input port of the second actor. The second actor contributes to the computation of a metric associated with one or more derivations of the first polymer.

It will be appreciated that the steps depicted in FIG. 8 represent a minimal set of steps that occur in a typical workflow. Typical workflows 66 include more than two actors. Furthermore, while the successive nature of actor execution has been emphasized in FIG. 8, it will be appreciated that actors within the same workflow that do not rely, either directly or indirectly, on each other can be run concurrently provided that there are sufficient hardware resources to run such actors Exemplary Process. Referring to FIG. 10, an exemplary process in accordance with the present disclosure is provided. First an overview of the exemplary process is provided and then more details are given. In an overview of the exemplary process, a workflow definition and a configuration file for a workflow are each parsed. Then a flow directory for the workflow is created. Next, the workflow is registered with a first server. The input and output ports of the workflow are evaluated to create a topographical sort of workflow actions. Each action is submitted to a second server but placed in a hold state. Once all the actions have been submitted, the workflow is ready for execution.

Now that an overview of the exemplary process has been provided, more detail is given. The exemplary process given here corresponds to steps 802 through 806 of FIG. 8.

Step 1002. The first step is to parse the configuration file 68. In typical embodiments, this file is in an ASCII based text format and contains information about which workflow to run and what parameters to run it with. The contents of the configuration depend on specific workflow but every file has a common [workflow] section which has a type option that specifies the workflow type. The module corresponding to the workflow type is loaded from a predetermined namespace and a parameter parser is created from its parameters() function. The parser is used to parse and validate the rest of the values in the configuration file. If the parameters are valid for the workflow, the workflow actors defined by the file are utilized via the workflow's init() function. The relations between actor inputs and outputs are used to create a list of the actions.

If an error occurs at any part in this stage the command aborts without anything having been created on the file system or in the database. This is to ensure that ill-formed configuration files or poorly defined workflows don't pollute the file system and database.

Step 1004. Once the workflow configuration has been verified as valid, a directory, termed the ".flow" directory, is created for the workflow in a location requested by the user. The directory is used to store the server authorization information and any data files generated during workflow execution.

Step 1006. In step 1006 the workflow is registered with a status server. In some embodiments, the status server is a server other than system 10 of FIG. 1. In some embodiments, the status server is one or more modules running on system 10, such as status server module 58. In some embodiments, the workflow metadata is POSTed to the status server's/workflows/endpoint in order to register the workflow. In some embodiments, this request is not authenticated.

Step 1008. If the data of step 1006 is valid, the status server module 58 will return the authorization information required to authorize future requests concerning this workflow 66. In step 1008, this information is saved in the flow directory associated with the workflow. As illustrated in FIG. 19, each workflow directory contains two directories: log and data. The log and data directories each contain named directories, one for each action or post-processing step (e.g: metrics_table). These directories store the logs and data for the actions or post-processing steps. In the case of data, there is a further level of directories corresponding to each of the action's outputs. The log and output directories then contain files named 1 to N, where N is the last task number for the action.

Step 1010. In step 1010, a topographical sort of workflow actions is created in accordance with step 806 of FIG. 8. The action graph created during workflow initialization is transformed into a list that is in the order in which the actions are preferably to be submitted using a topographical sort as illustrated, for example, in FIG. 9.

Step 1012. A client creates a job request for each action based on its required resources and execution strategy. Such things as the grid engine job array, memory and runtime requests, and any other options that are to be passed to grid engine server module 44 with its job submission are considered. The jobs are submitted in the hold state to prevent any of them from executing before all job submissions have completed.

Steps 1014-1018. Each job request 904 is then sent to the grid engine server module 44 which returns a job identifier 906 for the successfully submitted job. The job request is updated with the job identifier 906 and then its information is sent to a data storage database. This process is repeated for each action, with the request for subsequent actions being updated with job dependencies for the actions required to precede it.

If submitting the job to the grid engine server module 44 fails, no further action is necessary. The jobs which have been submitted up until this point remain in the hold state and the submit process for the workflow is resumed in the future. If committing the job information to the database fails, then the system sends a request to the gird engine server module 44 to delete the job as there is no record of it being associated with the action. In the case of failure at this stage the entire process aborts.

Step 1020. After all the jobs have been submitted, a client sends a request to the grid engine server module 44 to release the holds on the jobs. At this point the workflow begins executing.

Visualizing Workflow Results. Systems and methods for running workflows have been described. Typically, in such workflows, a plurality of different atomic replacements, insertions or deletions (derivation) of a biopolymer are analyzed. For each such derivation, the workflows are capable of evaluating and quantifying several different metrics in order to quantify the effects of such derivations. In this way, the workflows generate a large amount of information. In typical embodiments, this information is stored in fields in a database that are highly addressable. Because of this, it is possible to mine the data using automated visualization techniques. Thus, advantageously, the present disclosure provides graphical tools for visualizing this information. Reference is made to FIGS. 12 through 18 which describe one such method for visualizing the information.

In accordance with FIGS. 1 and 12-18, the present disclosure provides a computer system 10 for identifying an effect of a plurality of derivations of one or more polymers. The computer system comprises at least one processor and memory storing at least one program for execution by the at least one processor. In accordance with FIG. 1, this at least one program is embodied as user interface/post-processing module 64. As disclosed above, the computer system 10 concurrently processes a plurality of workflow instances 46. A first workflow instance 46 in the plurality of workflow instances operates on input data including a set of three-dimensional coordinates $\{x_1, \ldots, x_N\}$ for a polymer or a derivation of the polymer. Such processing comprises executing a plurality of actors 200 associated with the first workflow instance 46. Each actor in the plurality of actors has at least one input port and at least one output port. The first workflow instance 46 defines an acyclic directed graph comprising a plurality of nodes and a plurality of edges. Each node in the plurality of nodes is an actor in the plurality of actors. Each edge in the plurality of edges corresponds to at least one of (i) an input port of an actor in the plurality of actors and (ii) an output port of an actor in the plurality of actors. The executing of the plurality of actors comprises executing actors in the plurality of actors in an order specified by the acyclic directed graph, thereby generating a plurality of metrics relating to an effect of a plurality of derivations of one or more polymers. The plurality of metrics is stored in fields of a database associated with the first workflow instance. Subsequently, a request from a user to view the plurality of metrics is received.

Figure 12:
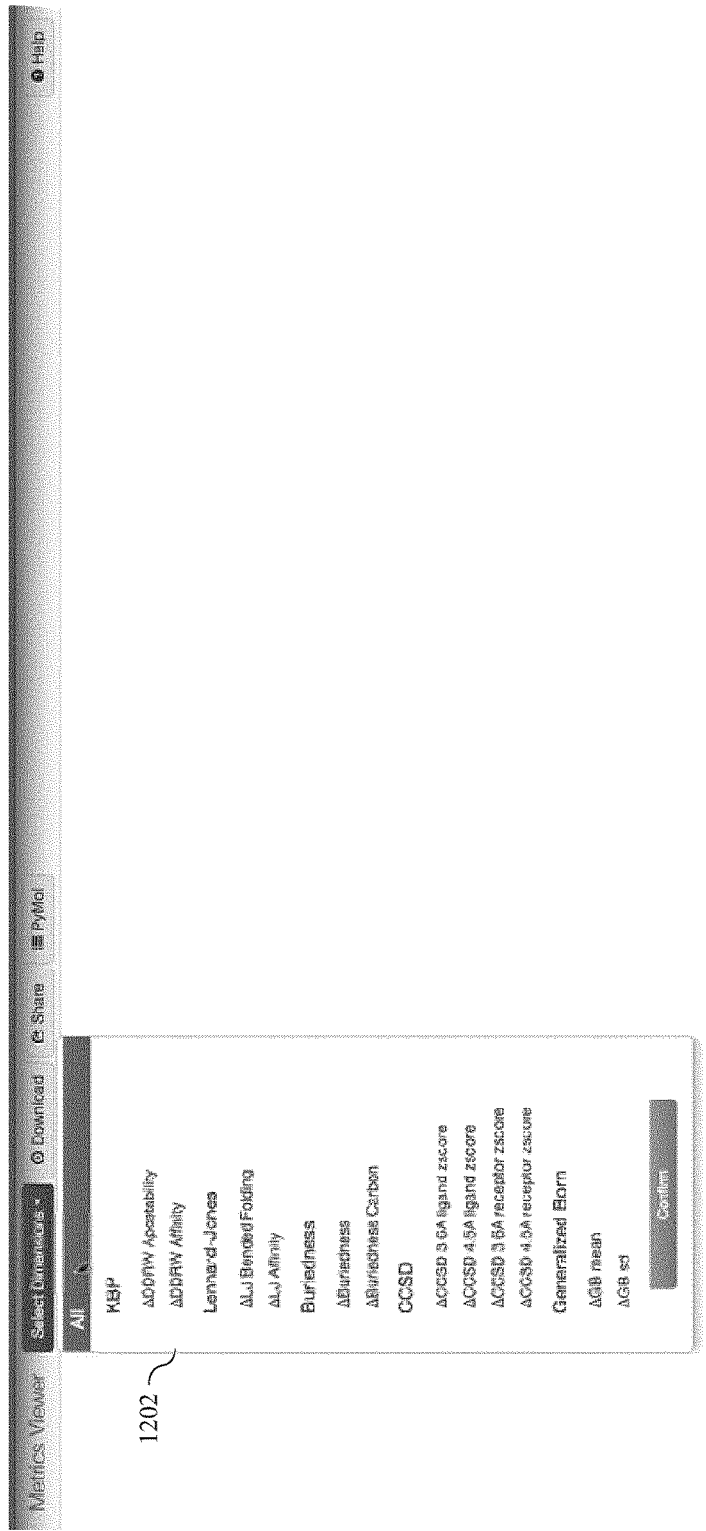
FIG. 12 illustrates a computer user interface providing a panel for selecting which metrics to display for a polymer analyzed by a workflow according to some embodiments
Figure 13:
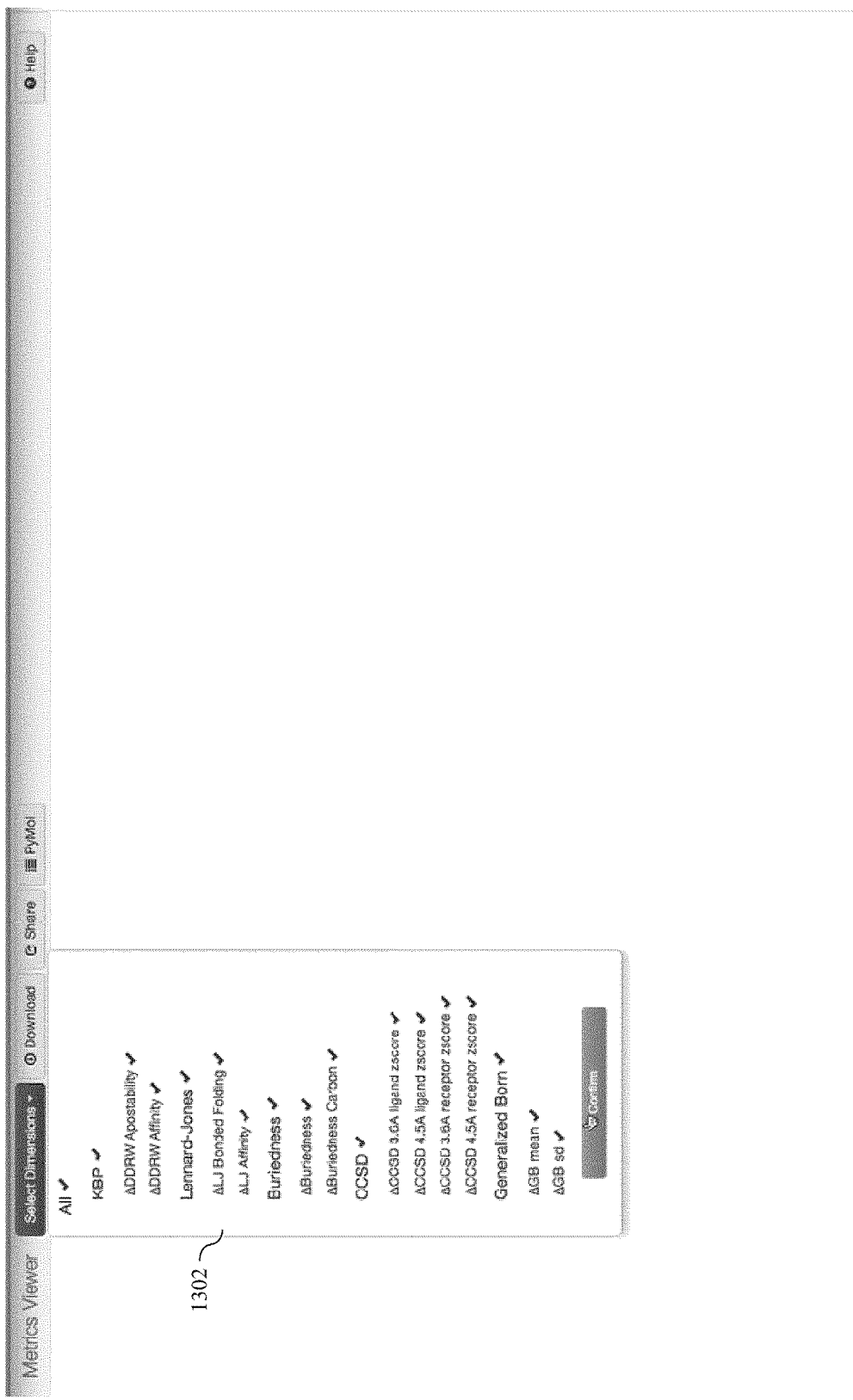
FIG. 13 illustrates a computer user interface providing the panel of FIG. 12 in which a user has selected all the available metrics to display for the polymer according to some embodiments.
Figure 14:
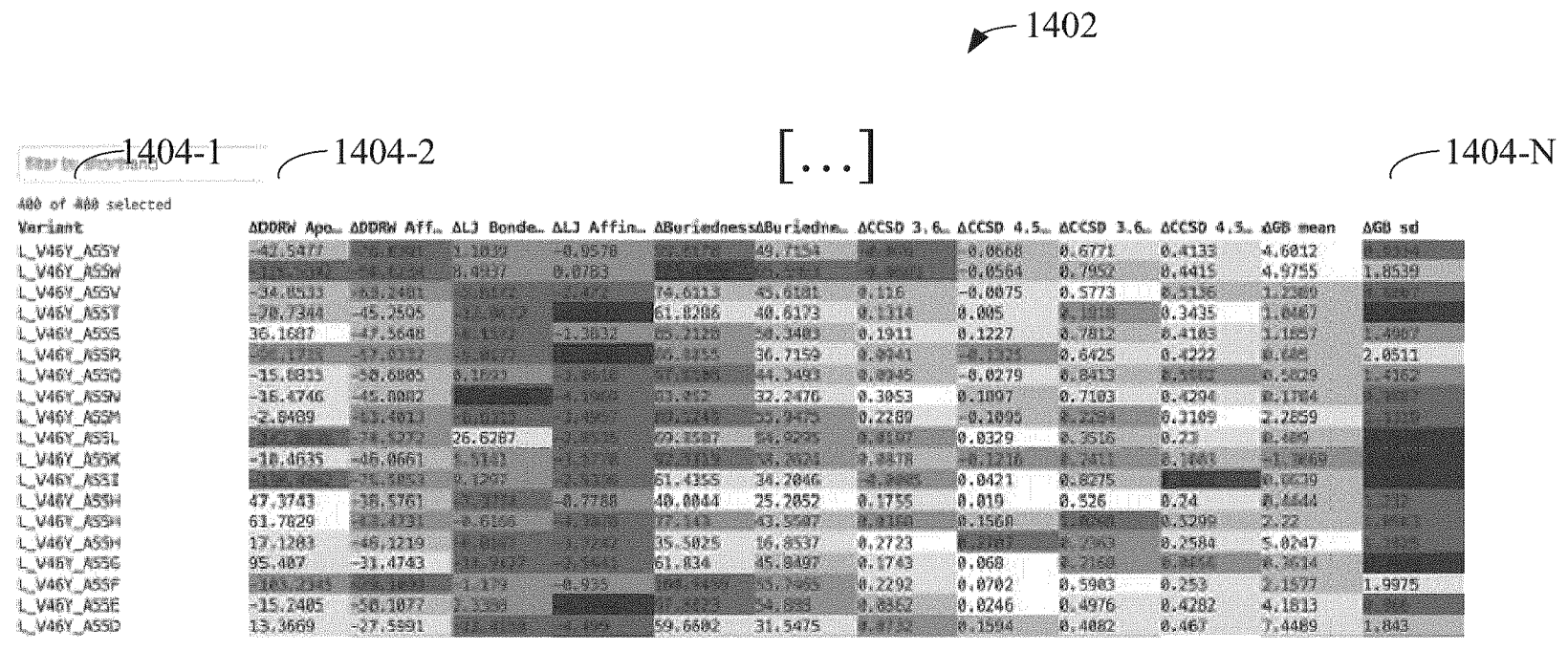

One example of how such a request is received is provided by FIG. 12. A user selects pull-down menu 1202 which displays a plurality of metrics that have been computed by a selected workflow instance 46. For instance, as illustrated in FIG. 13, the user has selected all of the metrics available for a given completed workflow. Referring to FIG. 14, responsive to this metric selection, a listing of a plurality of derivations of a polymer evaluated by the workflow instance 46 is provided in a multi-column table 1402. Table 1402 comprises a first column 1404-1 for an identity of a polymer derivation and a plurality of columns 1404-2 through 1404-N for the plurality of metrics. In other words, each column in the set $\{1404\text{-}2, 1404\text{-}3, \ldots, 1404\text{-}N\}$ is a value computed by a workflow instance 46 for a metric in a plurality of metrics for a polymer across a set of polymer derivations. Advantageously, referring to FIG. 15, displayed concurrently with table 1402 is a visualization of each metric in the plurality of metrics in a corresponding separate graph 1502 in a plurality of graphs.

The x-axis of each respective graph 1502 represents a range of scalar values for the metric represented by the respective graph. The y-axis represents the number of derivations in the plurality of derivations of the polymer evaluated by the workflow that have a given value or range of values for the metric represented by the respective graph. Thus, each bar in a respective graph 1502 in the plurality of graphs represents a group of derivations of a polymer that have the same or similar scalar value for the scalar represented by the respective graph. The height of a respective bar in the plurality of bars of a graph 1502 is proportional to the number of derivations represented by the bar. Thus, in the depicted embodiments, each graph 1502 includes a number of bars, each bar representing a number of derivations in the plurality of derivations. It will be appreciated by one of skill in the art that other graph types, other than bar graphs, could be used to represent the metrics of the plurality of derivations of the polymer evaluated by a given workflow instance 46 and all such graph types are within the scope of the present disclosure.

Figure 15:
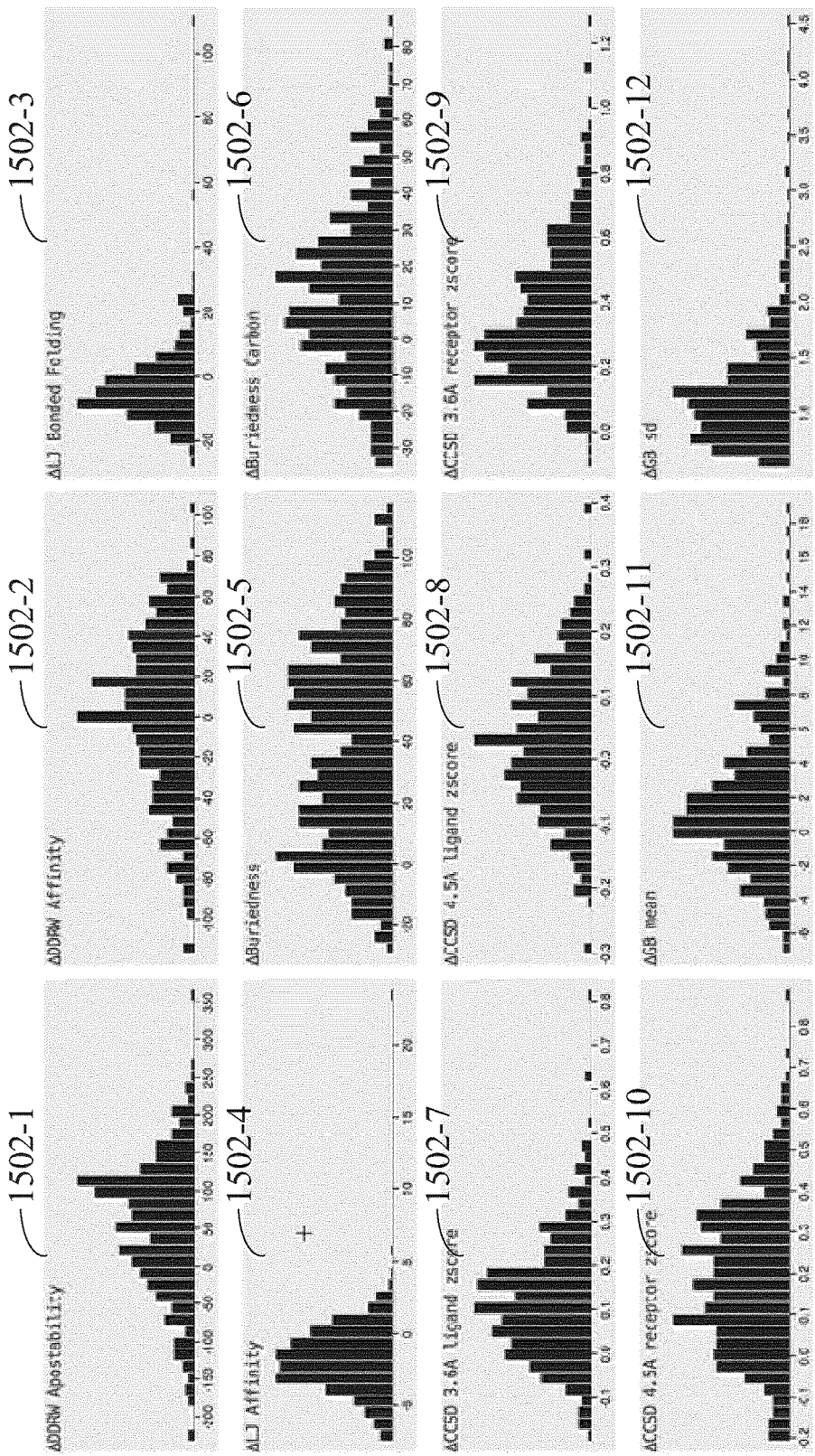
FIG. 15 illustrates a plurality of graphs, each respective graph in the plurality of graphs depicting a corresponding metric in a plurality of metrics across a plurality of derivations of a polymer that were processed by a workflow, the plurality of metrics selected using the panel of FIG. 13, and the plurality of derivations in the plurality of graphs corresponding to the plurality of derivations in the table of FIG. 14 according to some embodiments.
Figure 16:
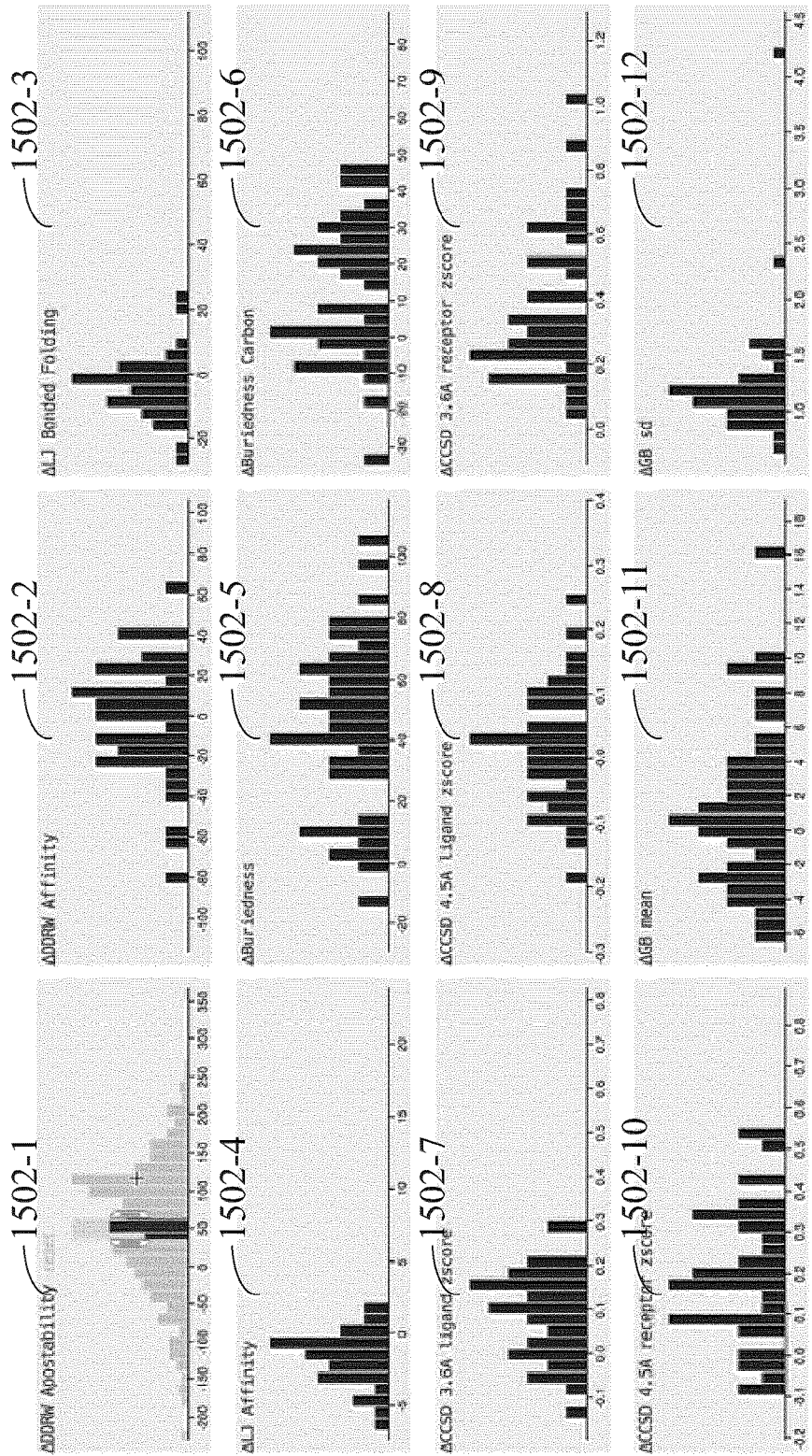
FIG. 16 illustrates how a first subset of derivations is selected by selecting a subset of derivations in a first graph in the plurality of graphs according to some embodiments.

In FIG. 15, all of the derivations available for a given workflow are displayed. Referring to FIG. 16, advantageously, a user can use a slider to select a subset of the bars in a first graph in the plurality of graphs, thereby selecting the corresponding polymer derivations represented by the subset of bars. For instance, in FIG. 16, a user uses a slider to select a subset of the polymer derivations depicted in graph 1502-1. In FIG. 16, the selected bars (derivations of the polymer) are indicated by a first color (e.g., solid blue) whereas the unselected bars are grayed out. One of skill in the art will appreciate that other schemes can be used to indicate which derivations in a given graph are selected and all such schemes are within the scope of the present disclosure.

Figure 17:
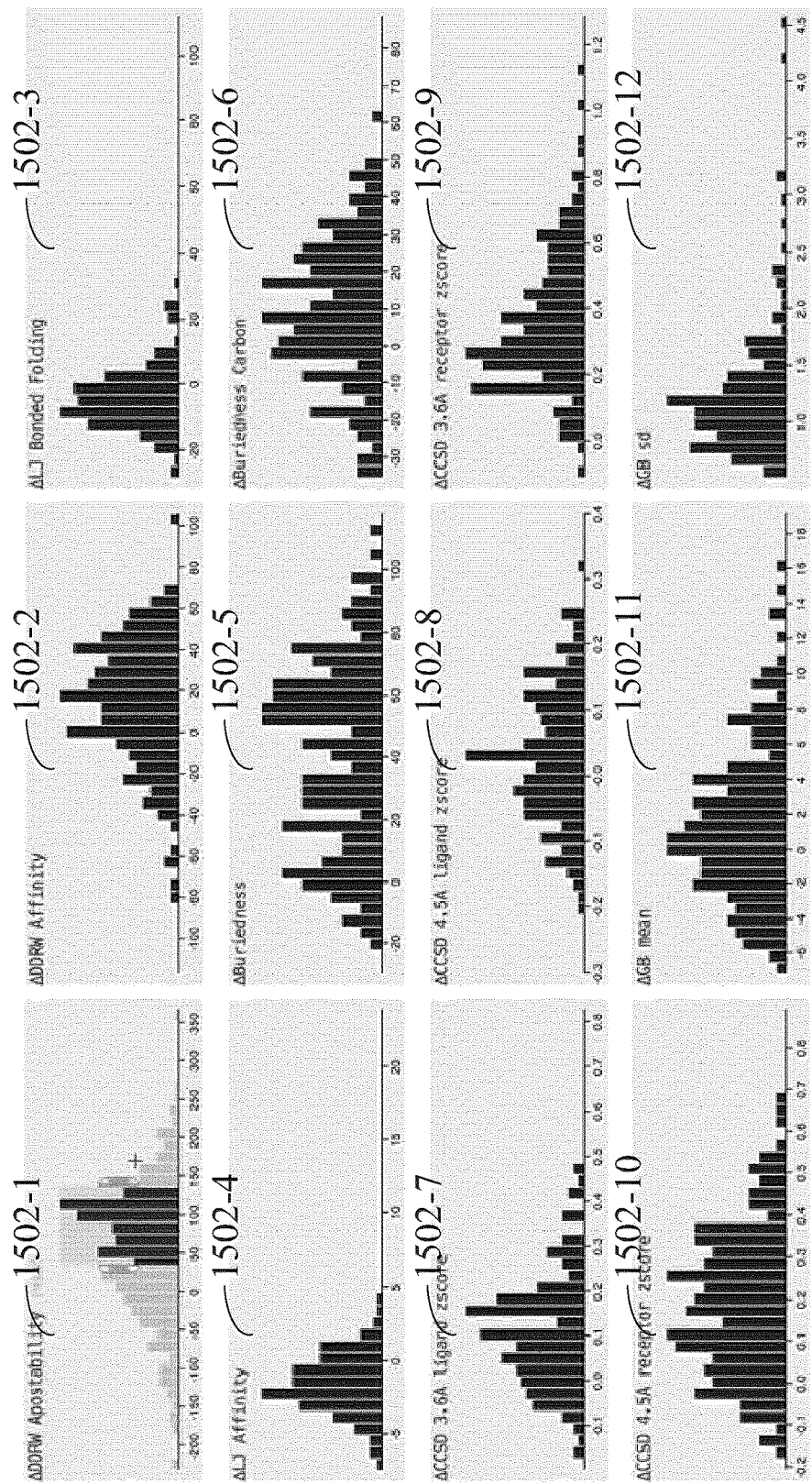
FIG. 17 illustrates how a second subset of derivations is selected by selecting a subset of derivations in a first graph in the plurality of graphs according to some embodiments.

As the user selects a subset of the polymer derivations in graph 1502-1, table 1402 is repeatedly updated without further user intervention to include only the derivations selected in graph 1502-1. Thus, as illustrated in FIGS. 15 and 16, the user is provided with a slider for each graph 1502 that can be used to explore the data set generated by a given workflow and to filter out those derivations that don't meet select metric criteria. In FIG. 17, for example, the user has relaxed the filter imposed in FIG. 16 by increasing the number of bars in graph 1502-1 that are selected. Responsive to this, table 1402 is updated without further user intervention to include the additional derivations selected in graph 1502-1.

The plurality of graphs 1502 can be used to impose a plurality of filters. For example, the user can build upon the filter created in FIG. 17 by defining a filter using graph 1502-2. Thus, referring to FIG. 18, only those derivations that have been selected by graph 1502-1 and graph 1502-2 are displayed in the table 1402. Thus, for example, the user can use the graphs to provide only those derivations that have suitable electrostatic energies but to also filter out from such derivations those derivations that have unfavorable hydrogen bonds. Advantageously, the plurality of graphs 1502 can be used by a user to chain together several different filters graphically to obtain a table 1402 that is a small subset of the total number of derivations evaluated by the workflow instance 46 and further represent the derivations that are more likely to be of interest and that should be evaluated in more detail. In one example, the derivations that remain listed in table 1402 after multiple filtering criterion have been applied are subjected to a second workflow that does a more detailed computational analysis. In another example, the derivations that remain listed in table 1402 after multiple filtering criterion have been applied are inspective graphically, and on a manual basis, by a user. In still another example, the derivations that remain listed in table 1402 after multiple filtering criterion have been applied are synthesized and subjected to one or more in vivo or in vitro assays.

Figure 18:
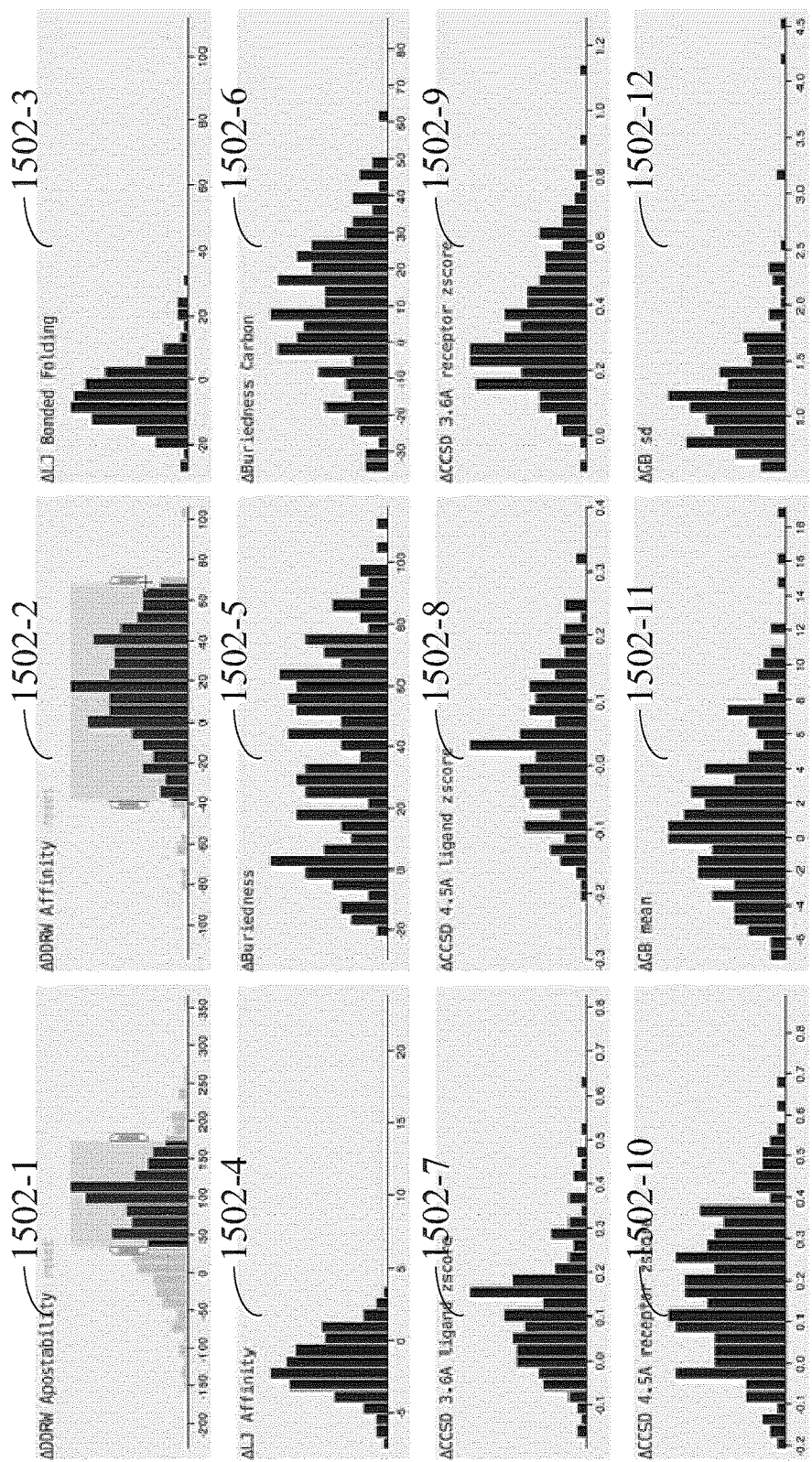
FIG. 18 illustrates how the second subset of FIG. 17 is further filtered using a second graph in the plurality of graphs according to some embodiments.

In some embodiments, the filtering criterion that are developed graphically using the sliders and that is illustrated by FIGS. 16 through 18 can be saved and applied against other workflows automatically without any requirement that the user toggle a series of graphical sliders to recreates the set of filtering criteria. In this way, the user can simply apply the same filters across a plurality of different workflows without having to do the same tedious filtering every time.

Additionally, when viewing table 1402 after the table has been filtered, the user has the option, in some embodiments, to visualize select derivations. Thus, in an exemplary process flow, a user uses a workflow instance 46 to evaluate ten thousand or more derivations of a polymer. Using graphs 1502 the user filters this set down to 200 derivations of the polymer. The user is now interested is seeing the derivations on the polymer structure. Rather than embarking on the tedious task of loading up these 200 structures into a graphical program such as Pymol one by one, and then trying to overlay them all on top of each other thereby achieving a visual mess that is difficult to interpret, the present disclosure provides an embedded three-dimensional viewer in some embodiments of the user interface/post-processing module 64 that operates seamlessly with the web page or other user form of user interface that displays graphs 1502 and table 1402. The user is provided with all the filtered derivations. The user selects which derivations are to be visualized and which metrics to visualize. For instance, when the user clicks on the metrics of interest, it brings up the viewer, with a three-dimensional model of the polymer displaying and metric of interest. For instance, in one example, the metric of interest is a hydrogen bond network. The user uses the graphs 1502 to reduce the number of derivations to fifty and wants to review the hydrogen bonding network in all fifty structures. The user requests the visualizer. When the visualizer opens up, the list of fifty derivations is provided. The user, for example, selects the top derivation on the list and so the structure of this derivation is displayed. The user reviews the hydrogen bonding network for this single derivation. On a side of the visualizer is provided the list of the other 49 derivations that can be viewed. If the user is interested in seeing several of them at the same time, the user can select several derivations from the list. For instance, in one embodiment the user selects multiple derivations by holding down the shift key and clicking on one, two, three, four, or more additional derivations. Upon selection, the additional derivations are overlayed in the same frame of reference on top of the originally selected derivation. Alternatively, if the user is interested in just seeing the last derivation by itself, not the first derivation, the user clicks on the last derivation and then the protein structure changes, so that the mutation in the last derivation is visible, along with its hydrogen bonding network. In this way, rather than requiring the user to use an external visualizer and try to find the specific position of interest in each derivation and then trying to measure distances and trying to find a clash, the user is presented with this information automatically. An advantageous use for this graphical tool is to visualize clashes. Such visual inspection is particularly adept at identifying small clashes that may arise when a large residue is substituted for a small residue. The visualization allows the user to see specifically how does clashes look. Such visualization is also useful to review hydrogen bonding networks. In such an application, the user performs a static structure analysis using the visualization tool. In some embodiments, the visualization parameters that are selected for a given workflow can be saved in the same manners as the selection criteria for graphs 1502 and applied against future workflows of the same type.

The methods illustrated in FIG. 8 may be governed by instructions that are stored in a computer readable storage medium and that are executed by at least one processor of at least one server. Each of the operations shown in FIG. 8 may correspond to instructions stored in a non-transitory computer memory or computer readable storage medium. In various implementations, the non-transitory computer readable storage medium includes a magnetic or optical disk storage device, solid state storage devices such as Flash memory, or other non-volatile memory device or devices. The computer readable instructions stored on the non-transitory computer readable storage medium may be in source code, assembly language code, object code, or other instruction format that is interpreted and/or executable by one or more processors.

Plural instances may be provided for components, operations or structures described herein as a single instance. Finally, boundaries between various components, operations, and data stores are somewhat arbitrary, and particular operations are illustrated in the context of specific illustrative configurations. Other allocations of functionality are envisioned and may fall within the scope of the implementation(s). In general, structures and functionality presented as separate components in the exemplary configurations may be implemented as a combined structure or component. Similarly, structures and functionality presented as a single component may be implemented as separate components. These and other variations, modifications, additions, and improvements fall within the scope of the implementation(s).

It will also be understood that, although the terms "first," "second," etc. may be used herein to describe various elements, these elements should not be limited by these terms. These terms are only used to distinguish one element from another. For example, a first contact could be termed a second contact, and, similarly, a second contact could be termed a first contact, which changing the meaning of the description, so long as all occurrences of the "first contact" are renamed consistently and all occurrences of the second contact are renamed consistently. The first contact and the second contact are both contacts, but they are not the same contact.

The terminology used herein is for the purpose of describing particular implementations only and is not intended to be limiting of the claims. As used in the description of the implementations and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in accordance with a determination" or "in response to detecting," that a stated condition precedent is true, depending on the context. Similarly, the phrase "if it is determined (that a stated condition precedent is true)" or "if (a stated condition precedent is true)" or "when (a stated condition precedent is true)" may be construed to mean "upon determining" or "in response to determining" or "in accordance with a determination" or "upon detecting" or "in response to detecting" that the stated condition precedent is true, depending on the context.

The foregoing description included example systems, methods, techniques, instruction sequences, and computing machine program products that embody illustrative implementations. For purposes of explanation, numerous specific details were set forth in order to provide an understanding of various implementations of the inventive subject matter. It will be evident, however, to those skilled in the art that implementations of the inventive subject matter may be practiced without these specific details. In general, well-known instruction instances, protocols, structures and techniques have not been shown in detail.

The foregoing description, for purpose of explanation, has been described with reference to specific implementations. However, the illustrative discussions above are not intended to be exhaustive or to limit the implementations to the precise forms disclosed. Many modifications and variations are possible in view of the above teachings. The implementations were chosen and described in order to best explain the principles and their practical applications, to thereby enable others skilled in the art to best utilize the implementations and various implementations with various modifications as are suited to the particular use contemplated.

What is claimed is:

1. A method of identifying an effect of a plurality of derivations of one or more polymers, the method comprising:
at a computer system having one or more processors and memory storing one or more programs to be executed by the one or more processors:
(A) concurrently processing a plurality of workflow instances, wherein a first workflow instance in the plurality of workflow instances operates on input data including a set of three-dimensional coordinates $\{x_1, \ldots, x_N\}$ for a first polymer or a derivation of the first polymer in the one or more polymers, wherein the processing comprises executing a plurality of actors associated with the first workflow instance, each actor in the plurality of actors having at least one input port and at least one output port, wherein the first workflow instance defines an acyclic directed graph comprising a plurality of nodes and a plurality of edges, each node in the plurality of nodes being an actor in the plurality of actors and each edge in the plurality of edges corresponding to at least one of (i) an input port of an actor in the plurality of actors and (ii) an output port of an actor in the plurality of actors, wherein a first edge in the plurality of edges is between a first node and a second node and a second edge in the plurality of edges is between the first node and a third node in the plurality of nodes, and wherein the executing the plurality of actors comprises executing actors in the plurality of actors in an order specified by the acyclic directed graph wherein the order specifies executing a first job request for the first node that precedes both a second job request for the second node and a third job request for the third node, and wherein the second job request and the third job request are eligible to be run concurrently, thereby generating a plurality of metrics relating to an effect of the plurality of derivations of the one or more polymers;
(B) storing the plurality of metrics in fields of a database associated with the first workflow instance; and
(C) responsive to a request from a user to view the plurality of metrics, (i) concurrently visualizing each metric in the plurality of metrics in a corresponding separate graph in a plurality of graphs, and (ii) listing the plurality of derivations of the first polymer in a multi-column table comprising a first column for an identity of a polymer derivation and a plurality of columns for the plurality of metrics.

2. The method of claim 1, the method further comprising:
(D) responsive to receiving a first selection of a first sub-range of a first graph in the plurality of graphs, limiting the derivations that are listed in the multi-column table to those in the first sub-range of the first graph.

3. The method of claim 2, the method further comprising:
(E) responsive to receiving a second selection of a second sub-range of a second graph in the plurality of graphs, limiting the derivations of the first polymer that are listed in the multi-column table to those that are in both the first sub-range of the first graph and the second sub-range of the second graph.

4. The method of claim 1, wherein each graph in the plurality of graphs is a histogram.

5. The method of claim 1, wherein the one or more polymers consists of the first polymer, the first polymer comprises a plurality of residues, and each derivation in the plurality of derivations is a replacement, insertion or deletion of one or more residues within the first polymer.

6. The method of claim 1, wherein a polymer in the one or more polymers is a protein, a polypeptide, a polynucleic acid, a polyribonucleic acid, a polysaccharide, or an assembly of any combination thereof.

7. The method of claim 1, wherein the input data for the first workflow instance specifies an atomic force field or a rotamer library.

8. The method of claim 1, wherein
each respective input port in each actor in the plurality of actors belongs to an input port class in a plurality of predetermined input port classes, and
each respective output port in each actor in the plurality of actors belongs to an output port class in a plurality of predetermined output port classes.

9. The method of claim 1, wherein an actor in the plurality of actors comprises a multi-input port that receives data from a first source and a second source.

10. The method of claim 9, wherein the first source is defined by the output port of another actor in the plurality of actors and the second source is a predetermined path to a file.

11. The method of claim 1, wherein an actor in the plurality of actors performs a task selected from the group consisting of a molecular dynamics algorithm, a structure refinement algorithm, a homology modeling algorithm, calculation of an accessible surface area term for a polymer, calculation of a potential energy term for a polymer, calculation of a solvent model for a polymer, calculation of a protein side-chain term for a polymer, calculation of a free volume term for a polymer, calculation of a packing efficiency term for a polymer, calculation of a number of interatomic contacts in a polymer, a structure relaxation and refinement algorithm, calculation of conformational substates and conformational sampling for a polymer, calculation of conformational flexibility, a Monte-Carlo or simulated annealing algorithm, calculation of a metric to determine a stability of a polymer, determination of a protonation state of a polymer, and a binding energy calculation for a polymer.

12. The method of claim 1, wherein the plurality of actors comprises three or more actors.

13. The method of claim 1, wherein the plurality of actors comprises five or more actors.

14. The method of claim 1, wherein the plurality of actors comprises ten or more actors.

15. The method of claim 1, wherein there is a many to one-relationship between an output port of a first actor in the plurality of actors and respective input ports of two or more actors in the plurality of actors other than the first actor.

16. The method of claim 1, wherein the first workflow instance produces a plurality of metric types for a plurality of derivations of the first polymer, wherein each derivation in the plurality of derivations includes one or more modifications to the primary sequence of the first polymer wherein each modification in the one or more modifications is selected from the group consisting of an insertion, deletion, or replacement in the primary sequence.

17. The method of claim 16, wherein the plurality of metric types comprises three or more metric types.

18. The method of claim 16, wherein the plurality of metric types comprises five or more metric types.

19. The method of claim 16, wherein the plurality of metric types comprises ten or more metric types.

20. The method of claim 16, wherein the plurality of derivations of the first polymer comprises one hundred or more derivations of the first polymer and wherein the plurality of metric types provides a separate evaluation of each derivation in the one hundred or more derivations.

21. The method of claim 16, wherein the plurality of derivations of the first polymer comprises one thousand or more derivations of the first polymer and wherein the plurality of metric types provides a separate evaluation of each derivation in the one thousand or more derivations.

22. The method of claim 16, wherein the plurality of derivations of the first polymer comprises ten thousand or more derivations of the first polymer and wherein the plurality of metric types provides a separate evaluation of each derivation in the ten thousand or more derivations.

23. The method of claim 16, wherein a metric type in the plurality of metric types is selected from the group consisting of a solvent accessible surface metric for all or portion of a polymer, a potential energy term for all or a portion of a polymer, a free volume term for all or a portion of a polymer, a packing efficiency term for all or a portion of a polymer, a number of interatomic contacts in all or a portion of a polymer, a binding energy calculation for all or a portion of a polymer, a stability calculation for all or a portion of a polymer, a calculation of the conformational flexibility of all or a portion of a polymer, a calculation of the packing density and inter-atom or inter-residue contacts for all or a portion of a polymer, a calculation of conformational freedom and alternate low energy states for all or a portion of a polymer.

24. The method of claim 16, wherein the first polymer comprises five hundred atoms.

25. The method of claim 16, wherein the first polymer comprises one thousand atoms.

26. The method of claim 1, wherein the acyclic directed graph is implicitly defined by a pattern of output ports specified by respective input ports in the plurality of actors.

27. The method of claim 1, wherein an input port of an actor in the plurality of actors is a single input port or a multi-input port.

\* \* \* \* \*